United States Patent
Stringer et al.

(10) Patent No.: US 11,918,603 B2
(45) Date of Patent: Mar. 5, 2024

(54) OCULAR LUBRICANT FORMULATIONS

(71) Applicant: HARROW IP, LLC, Nashville, TN (US)

(72) Inventors: William Stringer, Portland, OR (US); Michael Hanrahan, Portland, OR (US); Patrick H. Witham, Portland, OR (US)

(73) Assignee: Harrow IP, LLC, Nashville, TN (US)

( * ) Notice: Subject to any disclaimer, the term of this patent is extended or adjusted under 35 U.S.C. 154(b) by 66 days.

(21) Appl. No.: 17/268,256

(22) PCT Filed: Aug. 27, 2019

(86) PCT No.: PCT/US2019/048360
§ 371 (c)(1),
(2) Date: Feb. 12, 2021

(87) PCT Pub. No.: WO2020/046950
PCT Pub. Date: Mar. 5, 2020

(65) Prior Publication Data
US 2021/0315924 A1 Oct. 14, 2021

Related U.S. Application Data

(60) Provisional application No. 62/725,152, filed on Aug. 30, 2018.

(51) Int. Cl.
| | | |
|---|---|---|
| A61K 31/79 | (2006.01) | |
| A61F 9/00 | (2006.01) | |
| A61K 31/765 | (2006.01) | |
| A61K 47/02 | (2006.01) | |
| A61K 47/10 | (2017.01) | |
| A61K 47/18 | (2017.01) | |
| A61K 47/24 | (2006.01) | |
| A61K 47/26 | (2006.01) | |

(52) U.S. Cl.
CPC ............ *A61K 31/79* (2013.01); *A61F 9/0008* (2013.01); *A61K 31/765* (2013.01); *A61K 47/02* (2013.01); *A61K 47/10* (2013.01); *A61K 47/183* (2013.01); *A61K 47/24* (2013.01); *A61K 47/26* (2013.01)

(58) Field of Classification Search
CPC ...... A61K 47/02; A61K 47/183; A61K 47/32; A61K 47/24; A61K 9/0048; A61K 31/765; A61K 31/79; A61K 9/08; A61K 47/26; A61K 47/10; A61F 9/0008; A61P 27/04
See application file for complete search history.

(56) References Cited

U.S. PATENT DOCUMENTS

| | | | |
|---|---|---|---|
| 4,744,980 A * | 5/1988 | Holly | A61K 31/74 524/557 |
| 4,920,158 A | 4/1990 | Murray et al. | |
| 4,976,969 A | 12/1990 | Plamondon | |
| 2004/0142038 A1 * | 7/2004 | Echols | A61P 27/02 424/486 |
| 2007/0297990 A1 * | 12/2007 | Shah | A61K 33/26 514/217.05 |
| 2009/0044397 A1 * | 2/2009 | Cohen | A61F 9/0017 604/294 |
| 2009/0270335 A1 * | 10/2009 | Holly | A61K 38/08 514/9.4 |
| 2011/0319399 A1 | 12/2011 | Miura et al. | |
| 2012/0150132 A1 * | 6/2012 | Cress | A61F 9/0026 604/290 |
| 2013/0156720 A1 | 6/2013 | Currie | |
| 2018/0098937 A1 * | 4/2018 | Horn | A61P 29/00 |

FOREIGN PATENT DOCUMENTS

| | | |
|---|---|---|
| WO | 2016/172712 | 10/2016 |

OTHER PUBLICATIONS

International Search Report issued in PCT/US2019/048360, dated Dec. 26, 2019.
Written Opinion of the International Search Authority issued in PCT/US2019/048360, dated Dec. 26, 2019.

* cited by examiner

*Primary Examiner* — Doan T Phan

(57) ABSTRACT

Provided herein are formulations and compositions for ocular diseases or disorders such as dry eye disease. Further provided herein are methods for manufacturing ocular formulations and compositions.

22 Claims, 6 Drawing Sheets

OCULAR LUBRICANT FORMULATIONS

CROSS-REFERENCE TO RELATED APPLICATION

This International Application claims the benefit of U.S. Provisional Application No. 62/725,152 filed Aug. 30, 2018, the disclosure of which is expressly incorporated by reference herein in its entirety.

BACKGROUND

Millions of individuals suffer from an ocular disease or disorder costing billions of dollars a year in healthcare. For example, dry eye disease alone affects 20 million individuals. Dry eye may be a result of damaged tear film that no longer functions.

BRIEF SUMMARY

Provided herein are compositions comprising: (a) povidone; (b) fully hydrolyzed polyvinyl alcohol; and (c) partially hydrolyzed polyvinyl alcohol; wherein the composition is preservative free. Further provided herein are compositions, wherein a concentration of the povidone is about 1% to about 5%. Further provided herein are compositions, wherein a concentration of the fully hydrolyzed polyvinyl alcohol is about 0.5% to about 5%. Further provided herein are compositions, wherein a concentration of the partially hydrolyzed polyvinyl alcohol is about 0.5% to about 5%. Further provided herein are compositions, wherein a concentration of the fully hydrolyzed polyvinyl alcohol and the partially hydrolyzed polyvinyl alcohol is no more than about 4%. Further provided herein are compositions, wherein the fully hydrolyzed polyvinyl alcohol has a molecular weight in a range of about 80,000 to about 130,000 daltons. Further provided herein are compositions, wherein the partially hydrolyzed polyvinyl alcohol has a molecular weight in a range of about 10,000 to about 30,000 daltons. Further provided herein are compositions, further comprising sodium chloride, boric acid, disodium edetate dihydrate, potassium chloride, glycerin, ethyl alcohol, lecithin, polysorbate 80, hydrochloric acid, sodium hydroxide, water, or combinations thereof. Further provided herein are compositions, further comprising sodium chloride, boric acid, disodium edetate dihydrate, potassium chloride, behenyl alcohol, glyceryl stearate, lecithin, glycine Soja sterols, hydrochloric acid, sodium hydroxide, water, or combinations thereof. Further provided herein are compositions, wherein a concentration of sodium chloride is about 0.1% to about 1%. Further provided herein are compositions, wherein a concentration of boric acid is about 0.1% to about 1%. Further provided herein are compositions, wherein a concentration of disodium edetate dihydrate is about 0.01% to about 1%. Further provided herein are compositions, wherein a concentration of potassium chloride is about 0.01% to about 1%. Further provided herein are compositions, wherein a concentration of glycerin is about 0.001% to about 1%. Further provided herein are compositions, wherein a concentration of ethyl alcohol is about 0.001% to about 0.5%. Further provided herein are compositions, wherein a concentration of lecithin is about 0.001% to about 0.5%. Further provided herein are compositions, wherein a concentration of polysorbate 80 is about 0.01% to about 1%. Further provided herein are compositions, wherein a concentration of the behenyl alcohol, glyceryl stearate, lecithin, and glycine Soja sterols is about 0.01% to about 0.5%. Further provided herein are compositions, wherein a pH of the composition is no more than 6.6. Further provided herein are compositions, wherein a pH of the composition is no more than 6.5. Further provided herein are compositions, wherein a pH of the composition is 6.4. Further provided herein are compositions, wherein an osmolality of the composition is about 200 mOsm/kg to about 400 mOsm/kg. Further provided herein are compositions, wherein the composition is an ophthalmic composition.

Provided herein are compositions comprising: (a) povidone; (b) fully hydrolyzed polyvinyl alcohol, wherein the fully hydrolyzed polyvinyl alcohol has a molecular weight in a range of about 80,000 to about 130,000 daltons; and (c) partially hydrolyzed polyvinyl alcohol. Further provided herein are compositions, wherein a concentration of the povidone is about 1% to about 5%. Further provided herein are compositions, wherein a concentration of the fully hydrolyzed polyvinyl alcohol is about 0.5% to about 5%. Further provided herein are compositions, wherein a concentration of the partially hydrolyzed polyvinyl alcohol is about 0.5% to about 5%. Further provided herein are compositions, wherein the partially hydrolyzed polyvinyl alcohol has a molecular weight in a range of about 10,000 to about 30,000 daltons. Further provided herein are compositions, wherein a concentration of the fully hydrolyzed polyvinyl alcohol and the partially hydrolyzed polyvinyl alcohol is no more than about 4%. Further provided herein are compositions, further comprising sodium chloride, boric acid, disodium edetate dihydrate, potassium chloride, glycerin, ethyl alcohol, lecithin, polysorbate 80, hydrochloric acid, sodium hydroxide, water, or combinations thereof. Further provided herein are compositions, further comprising sodium chloride, boric acid, disodium edetate dihydrate, potassium chloride, behenyl alcohol, glyceryl stearate, lecithin, glycine Soja sterols, hydrochloric acid, sodium hydroxide, water, or combinations thereof. Further provided herein are compositions, wherein a concentration of sodium chloride is about 0.1% to about 1%. Further provided herein are compositions, wherein a concentration of boric acid is about 0.1% to about 1%. Further provided herein are compositions, wherein a concentration of disodium edetate dihydrate is about 0.01% to about 1%. Further provided herein are compositions, wherein a concentration of potassium chloride is about 0.01% to about 1%. Further provided herein are compositions, wherein a concentration of glycerin is about 0.001% to about 1%. Further provided herein are compositions, wherein a concentration of ethyl alcohol is about 0.001% to about 0.5%. Further provided herein are compositions, wherein a concentration of lecithin is about 0.001% to about 0.5%. Further provided herein are compositions, wherein a concentration of polysorbate 80 is about 0.01% to about 1%. Further provided herein are compositions, wherein a concentration of the behenyl alcohol, glyceryl stearate, lecithin, and glycine Soja sterols is about 0.01% to about 0.5%. Further provided herein are compositions, wherein a pH of the composition is no more than 6.6. Further provided herein are compositions, wherein a pH of the composition is no more than 6.5. Further provided herein are compositions, wherein a pH of the composition is 6.4. Further provided herein are compositions, wherein the composition is preservative free. Further provided herein are compositions, wherein an osmolality of the composition is about 200 mOsm/kg to about 400 mOsm/kg. Further provided herein are compositions, wherein the composition is an ophthalmic composition.

Provided herein are compositions comprising: (a) povidone; (b) fully hydrolyzed polyvinyl alcohol; and (c) partially hydrolyzed polyvinyl alcohol; wherein the composition has a pH of no more than 6.6. Further provided herein are compositions, wherein a concentration of the povidone is about 1% to about 5%. Further provided herein are compositions, wherein a concentration of the fully hydrolyzed polyvinyl alcohol is about 0.5% to about 5%. Further provided herein are compositions, wherein a concentration of the partially hydrolyzed polyvinyl alcohol is about 0.5% to about 5%. Further provided herein are compositions, wherein a concentration of the fully hydrolyzed polyvinyl alcohol and the partially hydrolyzed polyvinyl alcohol is no more than about 4%. Further provided herein are compositions, further comprising sodium chloride, boric acid, disodium edetate dihydrate, potassium chloride, glycerin, ethyl alcohol, lecithin, polysorbate 80, hydrochloric acid, sodium hydroxide, water, or combinations thereof. Further provided herein are compositions, further comprising sodium chloride, boric acid, disodium edetate dihydrate, potassium chloride, behenyl alcohol, glyceryl stearate, lecithin, glycine Soja sterols, hydrochloric acid, sodium hydroxide, water, or combinations thereof. Further provided herein are compositions, wherein a concentration of sodium chloride is about 0.1% to about 1%. Further provided herein are compositions, wherein a concentration of boric acid is about 0.1% to about 1%. Further provided herein are compositions, wherein a concentration of disodium edetate dihydrate is about 0.01% to about 1%. Further provided herein are compositions, wherein a concentration of potassium chloride is about 0.01% to about 1%. Further provided herein are compositions, wherein a concentration of glycerin is about 0.001% to about 1%. Further provided herein are compositions, wherein a concentration of ethyl alcohol is about 0.001% to about 0.5%. Further provided herein are compositions, wherein a concentration of lecithin is about 0.001% to about 0.5%. Further provided herein are compositions, wherein a concentration of polysorbate 80 is about 0.01% to about 1%. Further provided herein are compositions, wherein a concentration of the behenyl alcohol, glyceryl stearate, lecithin, and glycine Soja sterols is about 0.01% to about 0.5%. Further provided herein are compositions, wherein a pH of the composition is no more than 6.5. Further provided herein are compositions, wherein a pH of the composition is 6.4. Further provided herein are compositions, wherein an osmolality of the composition is about 200 mOsm/kg to about 400 mOsm/kg. Further provided herein are compositions, wherein the composition is an ophthalmic composition.

Provided herein are methods for producing a composition described herein, comprising: (a) preparing a first solution comprising the fully hydrolyzed polyvinyl alcohol and the partially hydrolyzed polyvinyl alcohol; (b) preparing a second solution comprising the povidone and one or more excipients; (c) adjusting a pH of the second solution to no more than 6.6; (d) combining the first solution and the second solution to create the composition; and (e) filter sterilizing the composition.

Provided herein are methods for producing a composition, comprising: (a) preparing a first solution comprising fully hydrolyzed polyvinyl alcohol and partially hydrolyzed polyvinyl alcohol; (b) preparing a second solution comprising povidone and one or more excipients; (c) adjusting a pH of the second solution to no more than 6.6; (d) combining the first solution and the second solution to create the composition; and (e) filter sterilizing the composition. Further provided herein are methods, wherein a concentration of the povidone is about 1% to about 5%. Further provided herein are methods, wherein a concentration of the fully hydrolyzed polyvinyl alcohol is about 0.5% to about 5%. Further provided herein are methods, wherein a concentration of the partially hydrolyzed polyvinyl alcohol is about 0.5% to about 5%. Further provided herein are methods, wherein a concentration of the fully hydrolyzed polyvinyl alcohol and the partially hydrolyzed polyvinyl alcohol is no more than about 4%. Further provided herein are methods, wherein the fully hydrolyzed polyvinyl alcohol has a molecular weight in a range of about 80,000 to about 130,000 daltons. Further provided herein are methods, wherein the partially hydrolyzed polyvinyl alcohol has a molecular weight in a range of about 10,000 to about 30,000 daltons. Further provided herein are methods, wherein the one or more excipients comprise sodium chloride, boric acid, disodium edetate dihydrate, potassium chloride, glycerin, ethyl alcohol, lecithin, polysorbate 80, or combinations thereof. Further provided herein are methods, wherein the one or more excipients comprise sodium chloride, boric acid, disodium edetate dihydrate, potassium chloride, behenyl alcohol, glyceryl stearate, lecithin, glycine Soja sterols, or combinations thereof. Further provided herein are methods, wherein a concentration of sodium chloride is about 0.1% to about 1%. Further provided herein are methods, wherein a concentration of boric acid is about 0.1% to about 1%. Further provided herein are methods, wherein a concentration of disodium edetate dihydrate is about 0.01% to about 1%. Further provided herein are methods, wherein a concentration of potassium chloride is about 0.01% to about 1%. Further provided herein are methods, wherein a concentration of glycerin is about 0.001% to about 1%. Further provided herein are methods, wherein a concentration of ethyl alcohol is about 0.001% to about 0.5%. Further provided herein are methods, wherein a concentration of lecithin is about 0.001% to about 0.5%. Further provided herein are methods, wherein a concentration of polysorbate 80 is about 0.01% to about 1%. Further provided herein are methods, wherein a concentration of the behenyl alcohol, glyceryl stearate, lecithin, and glycine Soja sterols is about 0.01% to about 0.5%. Further provided herein are methods, wherein the pH of the second solution is in no more than 6.5. Further provided herein are methods, wherein the pH of the second solution is in no more than 6.4. Further provided herein are methods, wherein the pH of the composition is no more than 6.6. Further provided herein are methods, wherein the pH of the composition is no more than 6.5. Further provided herein are methods, further comprising adjusting a pH of the composition following step (d). Further provided herein are methods, wherein an osmolality of the composition is about 200 mOsm/kg to about 400 mOsm/kg. Further provided herein are methods, wherein the composition is filtered through a filter of no more than 0.30 micron. Further provided herein are methods, wherein the composition is filtered through a filter of 0.22 micron. Further provided herein are methods, wherein the composition is filtered at a filtration rate of no more than 30 grams/minute. Further provided herein are methods, wherein the composition is filtered at a filtration rate of no more than 20 grams/minute. Further provided herein are methods, wherein the composition is preservative free. Further provided herein are methods, wherein the composition is an ophthalmic composition.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Definitions

Figure 1:
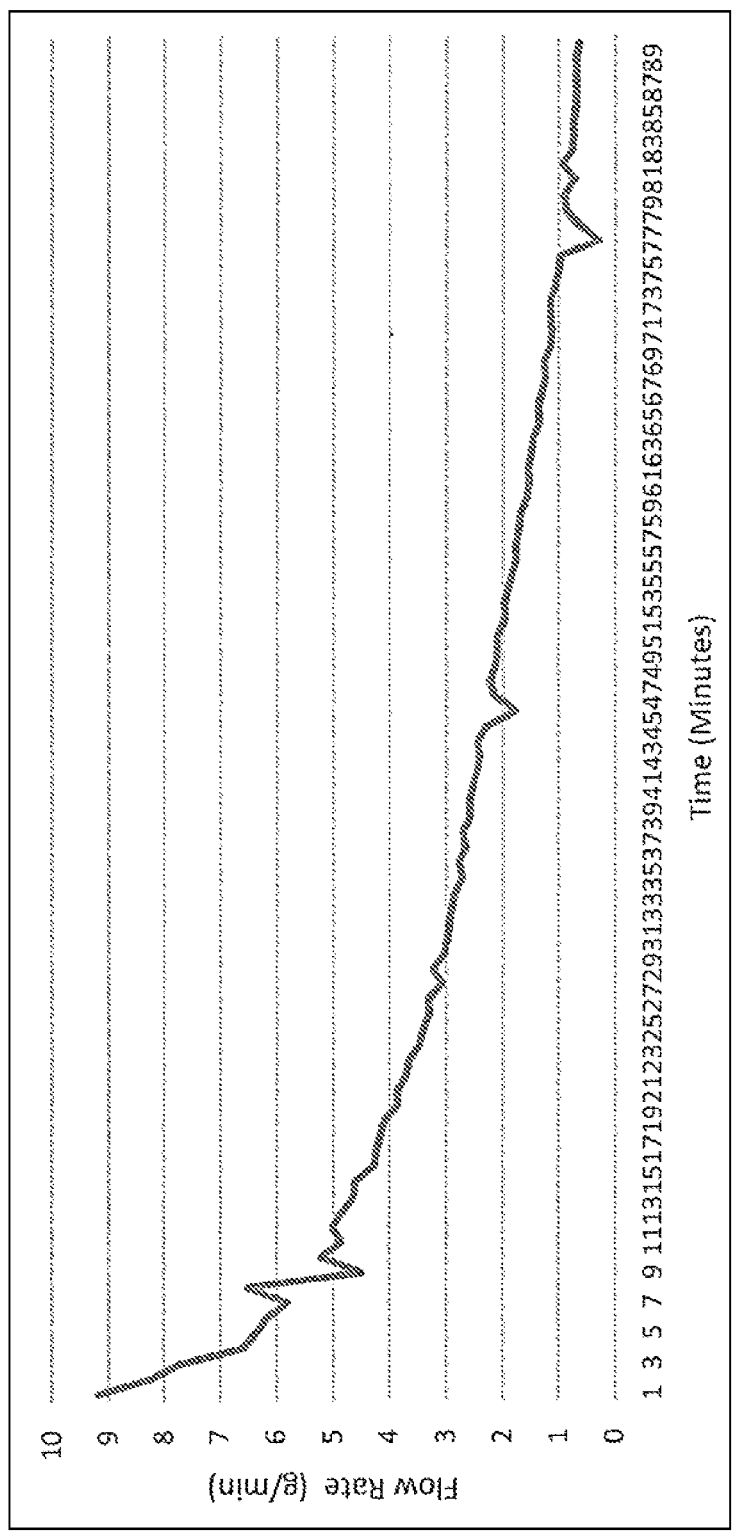
FIG. 1 is a graph of filtration flow rate for Exemplary Formulation 1 using the Cold Process. The x-axis is time (minutes) and the y-axis is flow rate (g/min.).

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges, in some embodiments, are independently included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

Formulations and Compositions

Described herein are formulations and compositions for ophthalmic use. Formulations and compositions as described herein are preservative free. Preservative free, in some embodiments, refers to an antimicrobial preservative. In some embodiments, the formulations and compositions comprise fully hydrolyzed polyvinyl alcohol, partially hydrolyzed polyvinyl alcohol, and povidone.

In some embodiments, formulations and compositions as described herein comprise fully hydrolyzed polyvinyl alcohol. In some embodiments, the fully hydrolyzed polyvinyl alcohol is provided at a concentration of at least or about 2, 4, 6, 8, 10, 12, 14, 16, 18, 20, 22, 24, 26, 28, 30, 32, 34, 36, 38, 40 or more than 40 mg/mL. In some embodiments, the fully hydrolyzed polyvinyl alcohol is provided at a concentration in a range of about 2 to about 40, about 4 to about 36, about 6 to about 34, about 10 to about 28, or about 16 to about 24 mg/mL. In some embodiments, the fully hydrolyzed polyvinyl alcohol is provided at a concentration of about 18 mg/mL. In some embodiments, the fully hydrolyzed polyvinyl alcohol is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (% wt/wt) or weight by volume (% wt/v). In some embodiments, the fully hydrolyzed polyvinyl alcohol is provided in a range of about 0.25% to about 10%, about 0.5% to about 8%, about 0.75% to about 6%, or about 1% to about 4% by weight (% wt/wt) or weight by volume (% wt/v). In some embodiments, the fully hydrolyzed polyvinyl alcohol is provided at about 1.80% by weight (% wt/wt) or weight by volume (% wt/v).

The fully hydrolyzed polyvinyl alcohol has a molecular weight of about 80,000 to about 130,000 daltons. In some embodiments, the molecular weight of the fully hydrolyzed polyvinyl alcohol is at least or about 60,000, 70,000, 80,000, 90,000, 100,000, 110,000, 120,000, 130,000, 140,000, 150,000, 160,000, 170,000, 180,000, 190,000, 200,000, or more than 200,000 daltons. In some embodiments, the molecular weight of the fully hydrolyzed polyvinyl alcohol is in a range of about 20,000 to about 200,000, about 40,000 to about 180,000, about 60,000 to about 160,000, or about 80,000 to about 140,000 daltons.

In some embodiments, formulations and compositions as described herein comprise partially hydrolyzed polyvinyl alcohol. In some embodiments, the partially hydrolyzed polyvinyl alcohol is provided at a concentration of at least or about 1, 2, 3, 4, 5, 6, 7, 8, 9, 10, 11, 12, 13, 14, 15, 16, 17, 18, 19, 20, or more than 20 mg/mL. In some embodiments, the partially hydrolyzed polyvinyl alcohol is provided at a concentration in a range of about 1 to about 20, about 2 to about 18, about 3 to about 15, about 4 to about 12, or about 5 to about 10 mg/mL. In some embodiments, the partially hydrolyzed polyvinyl alcohol is provided at a concentration of about 9 mg/mL. In some embodiments, the fully hydrolyzed polyvinyl alcohol is provided at least or about 0.05%, 0.10%, 0.25%, 0.50%, 0.75%, 0.90%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (% wt/wt) or weight by volume (% wt/v). In some embodiments, the partially hydrolyzed polyvinyl alcohol is provided in a range of about 0.25% to about 10%, about 0.5% to about 8%, about 0.75% to about 6%, or about 1% to about 4% by weight (% wt/wt) or weight by volume (% wt/v). In some embodiments, the partially hydrolyzed polyvinyl alcohol is provided at about 0.90% by weight (% wt/wt) or weight by volume (% wt/v).

The partially hydrolyzed polyvinyl alcohol, in some embodiments, has a molecular weight of about 10,000 to about 25,000 daltons. In some embodiments, the molecular weight of the partially hydrolyzed polyvinyl alcohol is at least or about 1,000, 2500, 5,000, 10,000, 15,000, 20,000, 25,000, 30,000, 35,000, 40,000, 45,000, 50,000, or more than 50,000 daltons. In some embodiments, the molecular weight of the partially hydrolyzed polyvinyl alcohol is in a range of about 1,000 to about 50,000, about 2,000 to about 40,000, about 4,000 to about 30,000, or about 8,000 to about 28,000 daltons.

In some embodiments, formulations and compositions as described herein comprise a concentration of fully hydrolyzed polyvinyl alcohol and partially hydrolyzed polyvinyl alcohol that is no more than 5%. In some embodiments, the concentration of fully hydrolyzed polyvinyl alcohol and partially hydrolyzed polyvinyl alcohol is at least or about 0.50%, 0.75%, 0.90%, 1.0%, 1.5%, 2.0%, 2.5%, 3.0%, 3.5%, 4.0%, 4.5%, 5.0%, 5.5%, 6.0%, 6.5%, 7.0%, 8%, or more than 8% weight (% wt/wt) or weight by volume (% wt/v). In some embodiments, the concentration of fully hydrolyzed polyvinyl alcohol and partially hydrolyzed polyvinyl alcohol is no more than about 2.7% weight (% wt/wt) or weight by volume (% wt/v).

In some embodiments, the fully hydrolyzed polyvinyl alcohol and partially hydrolyzed alcohol have a molecular weight in a range of about 10,000 to about 130,000 daltons. In some embodiments, the molecular weight of the fully hydrolyzed polyvinyl alcohol and partially hydrolyzed alcohol is at least or about 60,000, 70,000, 80,000, 90,000, 100,000, 110,000, 120,000, 130,000, 140,000, 150,000, 160,000, 170,000, 180,000, 190,000, 200,000, or more than 200,000 daltons. In some embodiments, the molecular weight of the fully hydrolyzed polyvinyl alcohol and partially hydrolyzed alcohol is in a range of about 20,000 to about 200,000, about 40,000 to about 180,000, about 60,000 to about 160,000, or about 80,000 to about 140,000 daltons.

In some embodiments, a potency of fully hydrolyzed polyvinyl alcohol, partially hydrolyzed polyvinyl alcohol, or a combination thereof is at least or about 80%, 85%, 90%, 95%, 100%, 110%, 120%, 125%, 130%, 140%, 150%, 160%, 170%, 180%, 190%, 200%, or more than 200%. In some embodiments, a potency of fully hydrolyzed polyvinyl alcohol, partially hydrolyzed polyvinyl alcohol, or a combination thereof is the potency prior to filtration. In some embodiments, a potency of fully hydrolyzed polyvinyl alcohol, partially hydrolyzed polyvinyl alcohol, or a combination thereof is the potency following filtration.

Formulations and compositions as described herein, in some embodiments, comprise povidone. In some embodiments, the povidone is provided at a concentration of at least or about 2, 4, 6, 8, 10, 12, 14, 16, 18, 20, 22, 24, 26, 28, 30, 32, 34, 36, 38, 40 or more than 40 mg/mL. In some embodiments, the povidone is provided at a concentration in a range of about 2 to about 40, about 4 to about 36, about 6 to about 34, about 10 to about 28, or about 16 to about 24 mg/mL. In some embodiments, the povidone is provided at a concentration of about 18 mg/mL. In some embodiments, the povidone is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (% wt/wt) or weight by volume (% wt/v). In some embodiments, the povidone is provided in a range of about 0.25% to about 10%, about 0.5% to about 8%, about 0.75% to about 6%, or about 1% to about 4% by weight (% wt/wt) or weight by volume (% wt/v). In some embodiments, the povidone is provided at about 2.0% by weight (% wt/wt) or weight by volume (% wt/v).

In some embodiments, a potency of povidone is at least or about 60%, 65%, 70%, 75%, 80%, 85%, 90%, 95%, 100%, 110%, 120%, 125%, 130%, 140%, 150%, 160%, 170%, 180%, or more than 180%. In some embodiments, a potency of povidone is the potency prior to filtration. In some embodiments, a potency of povidone is the potency following filtration.

Formulations and compositions as described herein, in some embodiments, further comprise additional reagents. For example, formulations and compositions as described herein comprise sodium chloride, boric acid, disodium edetate dihydrate, potassium chloride, glycerin, ethyl alcohol, lecithin, polysorbate 80, hydrochloric acid, sodium hydroxide, water, or combinations thereof. In some embodiments, formulations and compositions as described herein further comprise sodium chloride, boric acid, disodium edetate dihydrate, potassium chloride, behenyl alcohol, glyceryl stearate, lecithin, glycine Soja sterols, hydrochloric acid, sodium hydroxide, water, or combinations thereof.

In some embodiments, formulations and compositions as described herein comprise sodium chloride. In some embodiments, the sodium chloride is provided at a concentration of at least or about 0.05, 0.1, 0.2, 0.25, 0.3, 0.35, 0.4, 0.45, 0.5, 0.55, 0.60, 0.65, 0.70, 0.75, 0.80, 0.85, 0.90, 0.95, 1, 1.5, 2, 2.5, 3, 3.5, 4, 4.5, 5, 5.5, 6, 6.5, 7, 7.5, 8, 8.5, 9, 9.5, 10, or more than 10 mg/mL. In some embodiments, the sodium chloride is provided in a range of about 0.05 to about 4, about 0.2 to about 2, about 0.3 to about 1, or about 0.5 to about 0.75 mg/mL. In some embodiments, the sodium chloride is provided in a range of about 1 to about 10, about 2 to about 8, or about 4 to about 6 mg/mL. In some embodiments, the sodium chloride is provided at least or about 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% weight (% wt/wt) or weight by volume (% wt/v). In some embodiments, the sodium chloride is provided in a range of about 0.25% to about 10%, about 0.5% to about 8%, about 0.75% to about 6%, or about 1% to about 4% by weight (% wt/wt) or weight by volume (% wt/v). In some embodiments, the sodium chloride is provided at about 0.5% by weight (% wt/wt) or weight by volume (% wt/v).

In some embodiments, formulations and compositions as described herein comprise boric acid. In some embodiments, the boric acid is provided at a concentration of at least or about 0.05, 0.1, 0.2, 0.25, 0.3, 0.35, 0.4, 0.45, 0.5, 0.55, 0.60, 0.65, 0.70, 0.75, 0.80, 0.85, 0.90, 0.95, 1, 1.5, 2, 2.5, 3, 3.5, 4, or more than 4 mg/mL. In some embodiments, the boric acid is provided in a range of about 0.05 to about 4, about 0.2 to about 2, about 0.3 to about 1, or about 0.5 to about 0.75 mg/mL. In some embodiments, the boric acid is provided at least or about 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% weight (% wt/wt) or weight by volume (% wt/v). In some embodiments, the boric acid is provided in a range of about 0.01% to about 10%, about 0.02% to about 8%, about 0.04% to about 6%, about 0.08% to about 5%, or about 0.1% to about 2% weight (% wt/wt) or weight by volume (% wt/v). In some embodiments, the boric acid is provided at about 0.1% to about 1% by weight (% wt/wt) or weight by volume (% wt/v). In some embodiments, the boric acid is provided at about 0.2% by weight (% wt/wt) or weight by volume (% wt/v).

In some embodiments, formulations and compositions as described herein comprise disodium edetate dihydrate. In some embodiments, the disodium edetate dihydrate is provided at a concentration of at least or about 0.05, 0.1, 0.2, 0.25, 0.3, 0.35, 0.4, 0.45, 0.5, 0.55, 0.60, 0.65, 0.70, 0.75, 0.80, 0.85, 0.90, 0.95, 1, 1.5, 2, 2.5, 3, 3.5, 4, or more than 4 mg/mL. In some embodiments, the disodium edetate dihydrate is provided in a range of about 0.05 to about 4, about 0.2 to about 2, about 0.3 to about 1, or about 0.5 to about 0.75 mg/mL. In some embodiments, the disodium edetate dihydrate is provided at least or about 0.01%, 0.02%, 0.03%, 0.04%, 0.05%, 0.06%, 0.07%, 0.08%, 0.09%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% weight (% wt/wt) or weight by volume (% wt/v). In some embodiments, the disodium edetate dihydrate is provided in a range of about 0.01% to about 10%, about 0.02% to about 8%, about 0.04% to about 6%, about 0.08% to about 5%, or about 0.1% to about 2% weight (% wt/wt) or weight by volume (% wt/v). In some embodiments, the disodium edetate dihydrate is provided at about 0.01% to about 1% by weight (% wt/wt) or weight by volume (% wt/v). In some embodiments, the disodium edetate dihydrate is provided at about 0.1% by weight (% wt/wt) or weight by volume (% wt/v).

In some embodiments, formulations and compositions as described herein comprise potassium chloride. In some embodiments, the potassium chloride is provided at a concentration of at least or about 0.05, 0.1, 0.2, 0.25, 0.3, 0.35, 0.4, 0.45, 0.5, 0.55, 0.60, 0.65, 0.70, 0.75, 0.80, 0.85, 0.90, 0.95, 1, 1.5, 2, 2.5, 3, 3.5, 4, or more than 4 mg/mL. In some embodiments, the potassium chloride is provided in a range of about 0.05 to about 4, about 0.2 to about 2, about 0.3 to about 1, or about 0.5 to about 0.75 mg/mL. In some embodiments, the potassium chloride is provided at least or about 0.01%, 0.02%, 0.03%, 0.04%, 0.05%, 0.06%, 0.07%, 0.08%, 0.09%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% weight (% wt/wt) or weight by volume (% wt/v). In some embodiments, the potassium chloride is provided in a range of about 0.01% to about 10%, about 0.02% to about 8%, about 0.04% to about 6%, about 0.08% to about 5%, or about 0.1% to about 2% weight (% wt/wt) or weight by volume (% wt/v). In some embodiments, the potassium chloride is provided at about 0.01% to about 1% by weight (% wt/wt) or weight by volume (% wt/v). In some embodiments, the potassium chloride is provided at about 0.08% by weight (% wt/wt) or weight by volume (% wt/v).

In some embodiments, formulations and compositions as described herein comprise glycerin. In some embodiments, the glycerin is provided at a concentration of at least or about 0.05, 0.1, 0.2, 0.25, 0.3, 0.35, 0.4, 0.45, 0.5, 0.55, 0.60, 0.65, 0.70, 0.75, 0.80, 0.85, 0.90, 0.95, 1, 1.5, 2, 2.5, 3, 3.5, 4, or more than 4 mg/mL. In some embodiments, the glycerin is provided in a range of about 0.05 to about 4, about 0.2 to about 2, about 0.3 to about 1, or about 0.5 to about 0.75 mg/mL. In some embodiments, the glycerin is provided at least or about 00.001%, 0.002%, 0.005%, 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% weight (% wt/wt) or weight by volume (% wt/v). In some embodiments, the glycerin is provided in a range of about 0.001% to about 6%, about 0.002% to about 4%, about 0.01% to about 3%, or about 0.02% to about 2% weight (% wt/wt) or weight by volume (% wt/v). In some embodiments, the glycerin is provided at about 0.001% to about 1% by weight (% wt/wt) or weight by volume (% wt/v). In some embodiments, the glycerin is provided at about 0.01% by weight (% wt/wt) or weight by volume (% wt/v).

In some embodiments, formulations and compositions as described herein comprise ethyl alcohol. The ethyl alcohol, in some embodiments, comprises at least 10%, 20%, 30%, 40%, 50%, 60%, 70%, 80%, 90%, 95%, or more than 95% alcohol. In some embodiments, the ethyl alcohol comprises about 96% alcohol. In some embodiments, the ethyl alcohol is provided at a concentration of at least or about 0.05, 0.1, 0.2, 0.25, 0.3, 0.35, 0.4, 0.45, 0.5, 0.55, 0.60, 0.65, 0.70, 0.75, 0.80, 0.85, 0.90, 0.95, 1, 1.5, 2, 2.5, 3, 3.5, 4, or more than 4 mg/mL. In some embodiments, the ethyl alcohol is provided in a range of about 0.05 to about 4, about 0.2 to about 2, about 0.3 to about 1, or about 0.5 to about 0.75 mg/mL. In some embodiments, the ethyl alcohol is provided at least or about 00.001%, 0.002%, 0.005%, 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% weight (% wt/wt) or weight by volume (% wt/v). In some embodiments, the ethyl alcohol is provided in a range of about 0.001% to about 6%, about 0.002% to about 4%, about 0.01% to about 3%, or about 0.02% to about 2% weight (% wt/wt) or weight by volume (% wt/v). In some embodiments, the ethyl alcohol is provided at about 0.001% to about 1% by weight (% wt/wt) or weight by volume (% wt/v). In some embodiments, the ethyl alcohol is provided at about 0.0025% by weight (% wt/wt) or weight by volume (% wt/v).

In some embodiments, formulations and compositions as described herein comprise lecithin. In some embodiments, the lecithin is provided at a concentration of at least or about 0.05, 0.1, 0.2, 0.25, 0.3, 0.35, 0.4, 0.45, 0.5, 0.55, 0.60, 0.65, 0.70, 0.75, 0.80, 0.85, 0.90, 0.95, 1, 1.5, 2, 2.5, 3, 3.5, 4, or more than 4 mg/mL. In some embodiments, the lecithin is provided in a range of about 0.05 to about 4, about 0.2 to about 2, about 0.3 to about 1, or about 0.5 to about 0.75 mg/mL. In some embodiments, the lecithin is provided at least or about 00.001%, 0.002%, 0.005%, 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% weight (% wt/wt) or weight by volume (% wt/v). In some embodiments, the lecithin is provided in a range of about 0.001% to about 6%, about 0.002% to about 4%, about 0.01% to about 3%, or about 0.02% to about 2% weight (% wt/wt) or weight by volume (% wt/v). In some embodiments, the lecithin is provided at about 0.001% to about 1% by weight (% wt/wt) or weight by volume (% wt/v). In some embodiments, the lecithin is provided at about 0.005% by weight (% wt/wt) or weight by volume (% wt/v).

In some embodiments, formulations and compositions as described herein comprise polysorbate 80. In some embodiments, the polysorbate 80 is provided at a concentration of at least or about 0.05, 0.1, 0.2, 0.25, 0.3, 0.35, 0.4, 0.45, 0.5, 0.55, 0.60, 0.65, 0.70, 0.75, 0.80, 0.85, 0.90, 0.95, 1, 1.5, 2, 2.5, 3, 3.5, 4, or more than 4 mg/mL. In some embodiments, the polysorbate 80 is provided in a range of about 0.05 to about 4, about 0.2 to about 2, about 0.3 to about 1, or about 0.5 to about 0.75 mg/mL. In some embodiments, the polysorbate 80 is provided at least or about 00.001%, 0.002%, 0.005%, 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% weight (% wt/wt) or weight by volume (% wt/v). In some embodiments, the polysorbate 80 is provided in a range of about 0.001% to about 6%, about 0.002% to about 4%, about 0.01% to about 3%, or about 0.02% to about 2% weight (% wt/wt) or weight by volume (% wt/v). In some embodiments, the polysorbate 80 is provided at about 0.01% to about 1% by weight (% wt/wt) or weight by volume (% wt/v). In some embodiments, the polysorbate 80 is provided at about 0.025% by weight (% wt/wt) or weight by volume (% wt/v).

In some embodiments, formulations and compositions as described herein comprise behenyl alcohol, glyceryl stearate, lecithin, and glycine Soja sterols. In some embodiments, the behenyl alcohol, glyceryl stearate, lecithin, and glycine Soja sterols is provided at a concentration of at least or about 0.05, 0.1, 0.2, 0.25, 0.3, 0.35, 0.4, 0.45, 0.5, 0.55, 0.60, 0.65, 0.70, 0.75, 0.80, 0.85, 0.90, 0.95, 1, 1.5, 2, 2.5, 3, 3.5, 4, or more than 4 mg/mL. In some embodiments, the behenyl alcohol, glyceryl stearate, lecithin, and glycine Soja sterols is provided in a range of about 0.05 to about 4, about 0.2 to about 2, about 0.3 to about 1, or about 0.5 to about 0.75 mg/mL. In some embodiments, the behenyl alcohol, glyceryl stearate, lecithin, and glycine Soja sterols is provided at least or about 00.001%, 0.002%, 0.005%, 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% weight (% wt/wt) or weight by volume (% wt/v). In some embodiments, the behenyl alcohol, glyceryl stearate, lecithin, and glycine Soja sterols is provided in a range of about 0.001% to about 6%, about 0.002% to about 4%, about 0.01% to about 3%, or about 0.02% to about 2% weight (% wt/wt) or weight by volume (% wt/v). In some embodiments, the behenyl alcohol, glyceryl stearate, lecithin, and glycine Soja sterols is provided at about 0.01% to about 0.5% by weight (% wt/wt) or weight by volume (% wt/v). In some embodiments, the behenyl alcohol, glyceryl stearate, lecithin, and glycine Soja sterols is provided at about 0.05% by weight (% wt/wt) or weight by volume (% wt/v).

In some embodiments, the formulations further include pH adjusting agents or buffering agents which include acids such as acetic, boric, citric, lactic, phosphoric and hydrochloric acids, bases such as sodium hydroxide, sodium phosphate, sodium borate, sodium citrate, sodium acetate, sodium lactate and tris-hydroxymethylaminomethane, and buffers such as citrate/dextrose, sodium bicarbonate and ammonium chloride. Such acids, bases and buffers are included in an amount required to maintain pH of the composition in an acceptable range. In some embodiments, the pH adjusting agent is sodium hydroxide. In some embodiments, the pH adjusting agent is hydrochloric acid.

The pH adjusting agent, in some embodiments, is used to adjust the pH to a suitable range. In some embodiments, the pH is adjusted to at least or about 6.1, 6.15, 6.2, 6.25, 6.3, 6.35, 6.4, 6.45, 6.5, 6.55, 6.6, 6.65, 6.7, 6.75, 6.8, 6.85, or 6.9. In some embodiments, the pH is adjusted to about 6.3, 6.35, 6.4, 6.45, 6.5, 6.55, 6.6, 6.65, 6.7, 6.75, 6.8, 6.85, or 6.9.

Described herein are formulations and compositions, in some embodiments, comprising a pH of about 6.6 to about 6.9. In some embodiments, the pH is 6.1, 6.15, 6.2, 6.25, 6.3, 6.35, 6.4, 6.45, 6.5, 6.55, 6.6, 6.65, 6.7, 6.75, 6.8, 6.85, or 6.9. In some embodiments, the pH is 6.3, 6.35, 6.4, 6.45, 6.5, 6.55, 6.6, 6.65, 6.7, 6.75, 6.8, 6.85, or 6.9. In some embodiments, the pH is in a range of 6.1 to 7.0 or 6.6 to 6.9.

In some embodiments, the formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions, suitable salts include sodium chloride, potassium chloride, sodium thiosulfate, sodium bisulfite and ammonium sulfate.

Described herein are formulations and compositions, wherein the osmolality, in some embodiments, is in a range of about 260 to about 330 mOsm/kg. In some embodiments, the osmolality is at least or about 100, 120, 140, 160, 180, 200, 220, 240, 260, 280, 300, 320, 340, 360, 380, 400, 420, 440, 460, 480, 500, or more than 500 mOsm/kg. In some embodiments, the osmolality is in a range of about 100 to about 600, about 120 to about 580, about 140 to about 560, about 160 to about 500, or about 200 to about 340 mOsm/kg.

Formulations and compositions as described herein, in some embodiments, is a clear solution. In some embodiments, the formulations and compositions are colorless. In some embodiments, the formulations and compositions are free of visible particles.

Described herein, in some embodiments, are formulations and compositions that are preservative free. Preservative free, in some embodiments, refers to an antimicrobial preservative. Exemplary antimicrobial preservative includes, but are not limited to, methyl, ethyl, propyl and butyl parabens; sorbic acid; sodium, potassium, and calcium sorbate; benzoic acid; sodium, potassium, and calcium benzoate; sodium metabisulfite, propylene glycol; BHT; BHA; benzaldehyde; essential oils; phenol; and mercury compounds. In some embodiments, the preservative is a chemical preservative.

In some embodiments, formulations and compositions as described herein comprise a suitable viscosity. In some embodiments, the viscosity is the viscosity of the formulations and compositions prior to filtration. In some embodiments, the viscosity is the viscosity of the formulations and compositions following filtration. The viscosity, in some embodiments, is at least or about 10, 15, 20, 25, 30, 35, 40, 45, 50, 55, 60, 65, 70, 75, 80, or more than 80 centipoise (cps). In some embodiments, the viscosity is in a range of about 10 to about 80, about 15 to about 75, about 20 to about 70, or about 30 to about 60 cps. In some embodiments, the viscosity is determined at about 25° C. In some embodiments, the viscosity is determined at about 10° C., 15° C., 20° C., 25° C., 30° C., 35° C., 40° C., 45° C., 50° C., or more than 50° C. For example, the viscosity is at least or about 10, 15, 20, 25, 30, 35, 40, 45, 50, 55, 60, 65, 70, 75, 80, or more than 80 centipoise (cps) at about 10° C., 15° C., 20° C., 25° C., 30° C., 35° C., 40° C., 45° C., 50° C., or more than 50° C.

In some embodiments, formulations and compositions as described herein comprise a suitable surface tension. In some embodiments, the surface tension is the surface tension of the formulations and compositions prior to filtration. In some embodiments, the surface tension is the surface tension of the formulations and compositions following filtration. In some embodiments, the surface tension is at least or about 10, 15, 20, 25, 30, 35, 40, 45, 50, 55, 60, 65, 70, 75, 80, or more than 80 dynes/centimeter. In some embodiments, the surface tension is in a range of about 10 to about 80, about 15 to about 75, about 20 to about 70, or about 30 to about 60 dynes/centimeter.

In some embodiments, the formulations and compositions include, but are not limited to, sugars like trehalose, sucrose, mannitol, maltose, glucose, or salts like potassium phosphate, sodium citrate, ammonium sulfate and/or other agents such as heparin to increase the solubility and in vivo stability.

In some embodiments, the formulations and compositions further include diluents which are used to stabilize compounds because they can provide a more stable environment. Salts dissolved in buffered solutions (which also can provide pH control or maintenance) are utilized as diluents in the art, including, but not limited to a phosphate buffered saline solution. In certain instances, diluents increase bulk of the composition to facilitate compression or create sufficient bulk for homogenous blend for capsule filling. Such compounds include, but are not limited to, lactose, starch, mannitol, sorbitol, dextrose, microcrystalline cellulose such as Avicel®, dibasic calcium phosphate, dicalcium phosphate dihydrate, tricalcium phosphate, calcium phosphate, anhydrous lactose, spray-dried lactose, pregelatinized starch, compressible sugar, such as Di-Pac® (Amstar), mannitol, hydroxypropylmethylcellulose, hydroxypropylmethylcellulose acetate stearate, sucrose-based diluents, confectioner's sugar, monobasic calcium sulfate monohydrate, calcium sulfate dihydrate, calcium lactate trihydrate, dextrates, hydrolyzed cereal solids, amylose, powdered cellulose, calcium carbonate, glycine, kaolin, mannitol, sodium chloride, inositol, bentonite, and the like.

Methods for Manufacture

Described herein are methods for manufacturing formulations and compositions as described herein. In some embodiments, the formulations and compositions are preservative free. In some embodiments, the formulations and compositions comprise fully hydrolyzed polyvinyl alcohol, partially hydrolyzed polyvinyl alcohol, and povidone.

Methods for manufacturing formulations and compositions as described herein, in some embodiments, comprises preparing a first solution comprising fully hydrolyzed polyvinyl alcohol and partially hydrolyzed polyvinyl alcohol; preparing a second solution comprising povidone and one or more excipients; adjusting a pH of the second solution to no more than 6.6; combining the first solution and the second solution to create the composition; and filter sterilizing the composition.

In some embodiments, the fully hydrolyzed polyvinyl alcohol and the partially hydrolyzed polyvinyl alcohol are compounded together to generate a solution of polyvinyl alcohols. In some embodiments, the fully hydrolyzed polyvinyl alcohol and the partially hydrolyzed polyvinyl alcohol are dispersed in an aqueous solution. In some embodiments, the aqueous solution is water. In some embodiments, each of the fully hydrolyzed polyvinyl alcohol and the partially hydrolyzed polyvinyl alcohol is provided at a concentration of at least or about 1, 2, 3, 4, 5, 6, 7, 8, 9, 10, 11, 12, 13, 14, 15, 16, 17, 18, 19, 20, or more than 20 mg/mL. In some embodiments, each of the fully hydrolyzed polyvinyl alcohol and the partially hydrolyzed polyvinyl alcohol is provided at a concentration in a range of about 1 to about 20, about 2 to about 18, about 3 to about 15, about 4 to about 12, or about 5 to about 10 mg/mL. In some embodiments, each of the fully hydrolyzed polyvinyl alcohol and the partially hydrolyzed polyvinyl alcohol is provided at a concentration of about 9 mg/mL. In some embodiments, each of the fully hydrolyzed polyvinyl alcohol and the partially hydrolyzed polyvinyl alcohol is provided at least or about 0.05%, 0.10%, 0.25%, 0.50%, 0.75%, 0.90%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (% wt/wt) or weight by volume (% wt/v). In some embodiments, each of the fully hydrolyzed polyvinyl alcohol and the partially hydrolyzed polyvinyl alcohol is provided in a range of about 0.25% to about 10%, about 0.5% to about 8%, about 0.75% to about 6%, or about 1% to about 4% by weight (% wt/wt) or weight by volume (% wt/v).

In some embodiments, following dissolution of the fully hydrolyzed polyvinyl alcohol and the partially hydrolyzed polyvinyl alcohol, the solution of polyvinyl alcohols is heated. In some embodiments, the solution of polyvinyl alcohols is heated to at least or about 70° C., 75° C., 80° C., 85° C., 90° C., 95° C., 100° C., 105° C., 110° C., 120° C., or more than 120° C. In some embodiments, the solution is heated to about 95° C. to about 100° C. In some embodiments, the solution of polyvinyl alcohols is heated to 92.5±2.5° C. The solution of polyvinyl alcohols, in some embodiments, is maintained at a temperate in a range of at least or about 70° C., 75° C., 80° C., 85° C., 90° C., 95° C., 100° C., 105° C., 110° C., 120° C., or more than 120° C. In some embodiments, the solution of polyvinyl alcohols is maintained in a range of about 80° C. to about 95° C.

In some embodiments, the povidone is prepared with one or more excipients. For example, the povidone is prepared with sodium chloride, potassium chloride, boric acid, and disodium edetate dehydrate. In some embodiments, the povidone is prepared with sodium chloride, potassium chloride, boric acid, disodium edetate dehydrate, or combinations thereof.

In some embodiments, the povidone is provided at a concentration of at least or about 2, 4, 6, 8, 10, 12, 14, 16, 18, 20, 22, 24, 26, 28, 30, 32, 34, 36, 38, 40 or more than 40 mg/mL. In some embodiments, the povidone is provided at a concentration in a range of about 2 to about 40, about 4 to about 36, about 6 to about 34, about 10 to about 28, or about 16 to about 24 mg/mL. In some embodiments, the povidone is provided at a concentration of about 18 mg/mL. In some embodiments, the povidone is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (% wt/wt) or weight by volume (% wt/v). In some embodiments, the povidone is provided in a range of about 0.25% to about 10%, about 0.5% to about 8%, about 0.75% to about 6%, or about 1% to about 4% by weight (% wt/wt) or weight by volume (% wt/v). In some embodiments, the povidone is provided at about 2.0% by weight (% wt/wt) or weight by volume (% wt/v).

In some embodiments, the sodium chloride is provided at a concentration of at least or about 0.05, 0.1, 0.2, 0.25, 0.3, 0.35, 0.4, 0.45, 0.5, 0.55, 0.60, 0.65, 0.70, 0.75, 0.80, 0.85, 0.90, 0.95, 1, 1.5, 2, 2.5, 3, 3.5, 4, 4.5, 5, 5.5, 6, 6.5, 7, 7.5, 8, 8.5, 9, 9.5, 10, or more than 10 mg/mL. In some embodiments, the sodium chloride is provided in a range of about 0.05 to about 4, about 0.2 to about 2, about 0.3 to about 1, or about 0.5 to about 0.75 mg/mL. In some embodiments, the sodium chloride is provided in a range of about 1 to about 10, about 2 to about 8, or about 4 to about 6 mg/mL. In some embodiments, the sodium chloride is provided at least or about 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% weight (% wt/wt) or weight by volume (% wt/v). In some embodiments, the sodium chloride is provided in a range of about 0.25% to about 10%, about 0.5% to about 8%, about 0.75% to about 6%, or about 1% to about 4% by weight (% wt/wt) or weight by volume (% wt/v). In some embodiments, the sodium chloride is provided at about 0.5% by weight (% wt/wt) or weight by volume (% wt/v).

In some embodiments, the boric acid is provided at a concentration of at least or about 0.05, 0.1, 0.2, 0.25, 0.3, 0.35, 0.4, 0.45, 0.5, 0.55, 0.60, 0.65, 0.70, 0.75, 0.80, 0.85, 0.90, 0.95, 1, 1.5, 2, 2.5, 3, 3.5, 4, or more than 4 mg/mL. In some embodiments, the boric acid is provided in a range of about 0.05 to about 4, about 0.2 to about 2, about 0.3 to about 1, or about 0.5 to about 0.75 mg/mL. In some embodiments, the boric acid is provided at least or about 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% weight (% wt/wt) or weight by volume (% wt/v). In some embodiments, the boric acid is provided in a range of about 0.01% to about 10%, about 0.02% to about 8%, about 0.04% to about 6%, about 0.08% to about 5%, or about 0.1% to about 2% weight (% wt/wt) or weight by volume (% wt/v). In some embodiments, the boric acid is provided at about 0.1% to about 1% by weight (% wt/wt) or weight by volume (% wt/v). In some embodiments, the boric acid is provided at about 0.2% by weight (% wt/wt) or weight by volume (% wt/v).

In some embodiments, the disodium edetate dihydrate is provided at a concentration of at least or about 0.05, 0.1, 0.2, 0.25, 0.3, 0.35, 0.4, 0.45, 0.5, 0.55, 0.60, 0.65, 0.70, 0.75, 0.80, 0.85, 0.90, 0.95, 1, 1.5, 2, 2.5, 3, 3.5, 4, or more than 4 mg/mL. In some embodiments, the disodium edetate dihydrate is provided in a range of about 0.05 to about 4, about 0.2 to about 2, about 0.3 to about 1, or about 0.5 to about 0.75 mg/mL. In some embodiments, the disodium edetate dihydrate is provided at least or about 0.01%, 0.02%, 0.03%, 0.04%, 0.05%, 0.06%, 0.07%, 0.08%, 0.09%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% weight (% wt/wt) or weight by volume (% wt/v). In some embodiments, the disodium edetate dihydrate is provided in a range of about 0.01% to about 10%, about 0.02% to about 8%, about 0.04% to about 6%, about 0.08% to about 5%, or about 0.1% to about 2% weight (% wt/wt) or weight by volume (% wt/v). In some embodiments, the disodium edetate dihydrate is provided at about 0.01% to about 1% by weight (% wt/wt) or weight by volume (% wt/v). In some embodiments, the disodium edetate dihydrate is provided at about 0.1% by weight (% wt/wt) or weight by volume (% wt/v).

In some embodiments, the potassium chloride is provided at a concentration of at least or about 0.05, 0.1, 0.2, 0.25, 0.3, 0.35, 0.4, 0.45, 0.5, 0.55, 0.60, 0.65, 0.70, 0.75, 0.80, 0.85, 0.90, 0.95, 1, 1.5, 2, 2.5, 3, 3.5, 4, or more than 4 mg/mL. In some embodiments, the potassium chloride is provided in a range of about 0.05 to about 4, about 0.2 to about 2, about 0.3 to about 1, or about 0.5 to about 0.75 mg/mL. In some embodiments, the potassium chloride is provided at least or about 0.01%, 0.02%, 0.03%, 0.04%, 0.05%, 0.06%, 0.07%, 0.08%, 0.09%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% weight (% wt/wt) or weight by volume (% wt/v). In some embodiments, the potassium chloride is provided in a range of about 0.01% to about 10%, about 0.02% to about 8%, about 0.04% to about 6%, about 0.08% to about 5%, or about 0.1% to about 2% weight (% wt/wt) or weight by volume (% wt/v). In some embodiments, the potassium chloride is provided at about 0.01% to about 1% by weight (% wt/wt) or weight by volume (% wt/v). In some embodiments, the potassium chloride is provided at about 0.08% by weight (% wt/wt) or weight by volume (% wt/v).

A pH of the solution of povidone and the one more excipients is in a range of about 6.5 to about 6.9. In some embodiments, the pH is at least or about 6.1, 6.15, 6.2, 6.25, 6.3, 6.35, 6.4, 6.45, 6.5, 6.55, 6.6, 6.65, 6.7, 6.75, 6.8, 6.85, or 6.9. In some embodiments, the pH is 6.3, 6.35, 6.4, 6.45, 6.5, 6.55, 6.6, 6.65, 6.7, 6.75, 6.8, 6.85, or 6.9. In some embodiments, the pH is adjusted using a pH adjusting agent, for example sodium hydroxide or hydrochloric acid. In some embodiments, the pH is adjusted to at least or about 6.1, 6.15, 6.2, 6.25, 6.3, 6.35, 6.4, 6.45, 6.5, 6.55, 6.6, 6.65, 6.7, 6.75, 6.8, 6.85, or 6.9. In some embodiments, the pH is adjusted to a pH of 6.3, 6.35, 6.4, 6.45, 6.5, 6.55, 6.6, 6.65, 6.7, 6.75, 6.8, 6.85, or 6.9. In some embodiments, the pH is adjusted to pH in a range of 6.6 to 6.9. In some embodiments, the pH is adjusted to a pH in a range of 6.3 to 6.5.

In some embodiments, a solution comprising behenyl alcohol, glyceryl stearate, lecithin, and glycine Soja sterols is added. In some embodiments, the solution comprising behenyl alcohol, glyceryl stearate, lecithin, and glycine Soja sterols is added to the solution comprising the povidone and the one or more excipients. In some embodiments, the solution comprising behenyl alcohol, glyceryl stearate, lecithin, and glycine Soja sterols is added following combination of the polyvinyl alcohol solution and the povidone solution. In some embodiments, the combined solution of the polyvinyl alcohol solution and the povidone solution is cooled to room temperature prior to addition of the solution comprising behenyl alcohol, glyceryl stearate, lecithin, and glycine Soja sterols.

In some embodiments, the behenyl alcohol, glyceryl stearate, lecithin, and glycine Soja sterols is provided at a concentration of at least or about 0.05, 0.1, 0.2, 0.25, 0.3, 0.35, 0.4, 0.45, 0.5, 0.55, 0.60, 0.65, 0.70, 0.75, 0.80, 0.85, 0.90, 0.95, 1, 1.5, 2, 2.5, 3, 3.5, 4, or more than 4 mg/mL. In some embodiments, the behenyl alcohol, glyceryl stearate, lecithin, and glycine Soja sterols is provided in a range of about 0.05 to about 4, about 0.2 to about 2, about 0.3 to about 1, or about 0.5 to about 0.75 mg/mL. In some embodiments, the behenyl alcohol, glyceryl stearate, lecithin, and glycine Soja sterols is provided at least or about 00.001%, 0.002%, 0.005%, 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% weight (% wt/wt) or weight by volume (% wt/v). In some embodiments, the behenyl alcohol, glyceryl stearate, lecithin, and glycine Soja sterols is provided in a range of about 0.001% to about 6%, about 0.002% to about 4%, about 0.01% to about 3%, or about 0.02% to about 2% weight (% wt/wt) or weight by volume (% wt/v). In some embodiments, the behenyl alcohol, glyceryl stearate, lecithin, and glycine Soja sterols is provided at about 0.01% to about 0.5% by weight (% wt/wt) or weight by volume (% wt/v). In some embodiments, the behenyl alcohol, glyceryl stearate, lecithin, and glycine Soja sterols is provided at about 0.05% by weight (% wt/wt) or weight by volume (% wt/v).

In some embodiments, a solution comprising glycerin, ethyl alcohol, lecithin, and polysorbate 80 is added. In some embodiments, the solution comprising glycerin, ethyl alcohol, lecithin, and polysorbate 80 is added to the solution comprising the povidone and the one or more excipients. In some embodiments, the solution comprising glycerin, ethyl alcohol, lecithin, and polysorbate 80 is added following combination of the polyvinyl alcohol solution and the povidone solution. In some embodiments, the combined solution of the polyvinyl alcohol solution and the povidone solution is cooled to room temperature prior to addition of the solution comprising glycerin, ethyl alcohol, lecithin, and polysorbate 80.

In some embodiments, the glycerin is provided at a concentration of at least or about 0.05, 0.1, 0.2, 0.25, 0.3, 0.35, 0.4, 0.45, 0.5, 0.55, 0.60, 0.65, 0.70, 0.75, 0.80, 0.85, 0.90, 0.95, 1, 1.5, 2, 2.5, 3, 3.5, 4, or more than 4 mg/mL. In some embodiments, the glycerin is provided in a range of about 0.05 to about 4, about 0.2 to about 2, about 0.3 to about 1, or about 0.5 to about 0.75 mg/mL. In some embodiments, the glycerin is provided at least or about 00.001%, 0.002%, 0.005%, 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% weight (% wt/wt) or weight by volume (% wt/v). In some embodiments, the glycerin is provided in a range of about 0.001% to about 6%, about 0.002% to about 4%, about 0.01% to about 3%, or about 0.02% to about 2% weight (% wt/wt) or weight by volume (% wt/v). In some embodiments, the glycerin is provided at about 0.001% to about 1% by weight (% wt/wt) or weight by volume (% wt/v). In some embodiments, the glycerin is provided at about 0.01% by weight (% wt/wt) or weight by volume (% wt/v).

The ethyl alcohol, in some embodiments, comprises at least 10%, 20%, 30%, 40%, 50%, 60%, 70%, 80%, 90%, 95%, or more than 95% alcohol. In some embodiments, the ethyl alcohol comprises about 96% alcohol. In some embodiments, the ethyl alcohol is provided at a concentration of at least or about 0.05, 0.1, 0.2, 0.25, 0.3, 0.35, 0.4, 0.45, 0.5, 0.55, 0.60, 0.65, 0.70, 0.75, 0.80, 0.85, 0.90, 0.95, 1, 1.5, 2, 2.5, 3, 3.5, 4, or more than 4 mg/mL. In some embodiments, the ethyl alcohol is provided in a range of about 0.05 to about 4, about 0.2 to about 2, about 0.3 to about 1, or about 0.5 to about 0.75 mg/mL. In some embodiments, the ethyl alcohol is provided at least or about 00.001%, 0.002%, 0.005%, 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% weight (% wt/wt) or weight by volume (% wt/v). In some embodiments, the ethyl alcohol is provided in a range of about 0.001% to about 6%, about 0.002% to about 4%, about 0.01% to about 3%, or about 0.02% to about 2% weight (% wt/wt) or weight by volume (% wt/v). In some embodiments, the ethyl alcohol is provided at about 0.001% to about 1% by weight (% wt/wt) or weight by volume (% wt/v). In some embodiments, the ethyl alcohol is provided at about 0.0025% by weight (% wt/wt) or weight by volume (% wt/v).

In some embodiments, the lecithin is provided at a concentration of at least or about 0.05, 0.1, 0.2, 0.25, 0.3, 0.35, 0.4, 0.45, 0.5, 0.55, 0.60, 0.65, 0.70, 0.75, 0.80, 0.85, 0.90, 0.95, 1, 1.5, 2, 2.5, 3, 3.5, 4, or more than 4 mg/mL. In some embodiments, the lecithin is provided in a range of about 0.05 to about 4, about 0.2 to about 2, about 0.3 to about 1, or about 0.5 to about 0.75 mg/mL. In some embodiments, the lecithin is provided at least or about 00.001%, 0.002%, 0.005%, 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% weight (% wt/wt) or weight by volume (% wt/v). In some embodiments, the lecithin is provided in a range of about 0.001% to about 6%, about 0.002% to about 4%, about 0.01% to about 3%, or about 0.02% to about 2% weight (% wt/wt) or weight by volume (% wt/v). In some embodiments, the lecithin is provided at about 0.001% to about 1% by weight (% wt/wt) or weight by volume (% wt/v). In some embodiments, the lecithin is provided at about 0.005% by weight (% wt/wt) or weight by volume (% wt/v).

In some embodiments, the polysorbate 80 is provided at a concentration of at least or about 0.05, 0.1, 0.2, 0.25, 0.3, 0.35, 0.4, 0.45, 0.5, 0.55, 0.60, 0.65, 0.70, 0.75, 0.80, 0.85, 0.90, 0.95, 1, 1.5, 2, 2.5, 3, 3.5, 4, or more than 4 mg/mL. In some embodiments, the polysorbate 80 is provided in a range of about 0.05 to about 4, about 0.2 to about 2, about 0.3 to about 1, or about 0.5 to about 0.75 mg/mL. In some embodiments, the polysorbate 80 is provided at least or about 00.001%, 0.002%, 0.005%, 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% weight (% wt/wt) or weight by volume (% wt/v). In some embodiments, the polysorbate 80 is provided in a range of about 0.001% to about 6%, about 0.002% to about 4%, about 0.01% to about 3%, or about 0.02% to about 2% weight (% wt/wt) or weight by volume (% wt/v). In some embodiments, the polysorbate 80 is provided at about 0.01% to about 1% by weight (% wt/wt) or weight by volume (% wt/v). In some embodiments, the polysorbate 80 is provided at about 0.025% by weight (% wt/wt) or weight by volume (% wt/v).

Following combination of the polyvinyl alcohol solution, the povidone solution, and the solution comprising the behenyl alcohol, glyceryl stearate, lecithin, and glycine Soja sterols, the combined solution is filtered. In some embodiments, the combined solution comprising the polyvinyl alcohol solution, the povidone solution, and the solution comprising the glycerin, ethyl alcohol, lecithin, and polysorbate 80 is filtered. In some embodiments, the combined solution is filtered using a 0.1, 0.2, 0.3, 0.4, 0.5, 0.6, 0.7, 0.8, 0.9, 1.0, 1.1, 1.2, 1.3, 1.4, or more than 1.4 micron or um filter. In some embodiments, multiple filters are used.

In some embodiments, the combined solution is filtered using at least or about 10, 15, 20, 25, 30, 35, 40, 45, 50, 55, 60, or more than 60 psig of gas. In some embodiments, about 30 psig of gas is used to filter the combined solution. In some embodiments, the gas is nitrogen gas.

Formulations and compositions as described herein, in some embodiments, are filtered at rate of at least or about 5, 10, 15, 20, 25, 30, 35, 40 g/minute. In some embodiments, the formulations and compositions are filtered in a range of about 5 to about 40 or about 10 to about 30 g/minute. In some embodiments, the formulations and compositions are filtered at about 20 g/minute.

In some embodiments, formulations and compositions as described herein are analyzed for various parameters. Exemplary parameters include, but are not limited to, pH, product appearance, viscosity, osmolality, bioburden, bacteria aerobic, bacteria anaerobic, yeasts and molds, and filling weight.

Formulations and compositions manufactured by methods as described herein, in some embodiments, comprise a pH of about 6.6 to about 6.9. In some embodiments, the pH is 6.1, 6.15, 6.2, 6.25, 6.3, 6.35, 6.4, 6.45, 6.5, 6.55, 6.6, 6.65, 6.7, 6.75, 6.8, 6.85, or 6.9. In some embodiments, the pH is 6.3, 6.35, 6.4, 6.45, 6.5, 6.55, 6.6, 6.65, 6.7, 6.75, 6.8, 6.85, or 6.9. In some embodiments, the pH is in a range of 6.1 to 7.0 or 6.6 to 6.9.

In some embodiments, formulations and compositions as described herein comprise a suitable viscosity. In some embodiments, the viscosity is the viscosity of the formulations and compositions prior to filtration. In some embodiments, the viscosity is the viscosity of the formulations and compositions following filtration. The viscosity, in some embodiments, is at least or about 10, 15, 20, 25, 30, 35, 40, 45, 50, 55, 60, 65, 70, 75, 80, or more than 80 centipoise (cps). In some embodiments, the viscosity is in a range of about 10 to about 80, about 15 to about 75, about 20 to about 70, or about 30 to about 60 cps.

The osmolality, in some embodiments, is in a range of about 260 to about 330 mOsm/kg. In some embodiments, the osmolality is at least or about 100, 120, 140, 160, 180, 200, 220, 240, 260, 280, 300, 320, 340, 360, 380, 400, 420, 440, 460, 480, 500, or more than 500 mOsm/kg. In some embodiments, the osmolality is in a range of about 100 to about 600, about 120 to about 580, about 140 to about 560, about 160 to about 500, or about 200 to about 340 mOsm/kg.

Formulations and compositions as described herein, in some embodiments, comprise a bioburden, bacteria aerobic, bacteria anaerobic, yeasts and molds, or combinations thereof of no more than 10 colony forming units (CFU) per mL. In some embodiments, the bioburden, bacteria aerobic, bacteria anaerobic, yeasts and molds, or combinations thereof is at most or about 1, 2, 3, 4, 5, 6, 7, 8, 9, 10, 11, 12, 13, 14, or 15 CFUs/mL.

Methods for Treatment

Described herein, in some embodiments, are methods, compositions, and formulations comprising fully hydrolyzed polyvinyl alcohol, partially hydrolyzed polyvinyl alcohol, and povidone for use in a treatment of a disease or disorder. In some embodiments, the disease or disorder is an ocular disease or disorder. In some embodiments, the disease or disorder dry eye. In some embodiments, the methods, compositions, and formulations as described herein improve or replace damaged tear film.

Exemplary ocular diseases or disorder include, but are not limited to, inflammatory conjunctivitis, including allergic and giant papillary conjunctivitis, macular edema, uveitis, endophthalmitis, scleritis, corneal ulcers, dry eye syndrome, glaucoma, ischemic retinal disease, corneal transplant rejection, complications related to intraocular surgery such intraocular lens implantation and inflammation associated with cataract surgery, Behcet's disease, Stargardt disease, immune complex vasculitis, Fuch's disease, Vogt-Koyanagi-Harada disease, subretinal fibrosis, keratitis, vitreoretinal inflammation, ocular parasitic infestation/migration, retinitis pigmentosa, cytomegalovirus retinitis and choroidal inflammation. In some embodiments, the ocular diseases or disorders that are amendable to treatment by the methods and compositions provided herein include, without limitation, ectropion, lagophthalmos, blepharochalasis, ptosis, xanthelasma of the eyelid, parasitic infestation of the eyelid, dermatitis of the eyelid, dacryoadenitis, epiphora, dysthyroid exophthalmos, conjunctivitis, scleritis, keratitis, corneal ulcer, corneal abrasion, snow blindness, arc eye, Thygeson's superficial punctate keratopathy, corneal neovascularization, Fuchs' dystrophy, keratoconus, keratoconjunctivitis sicca, iritis, uveitis, sympathetic ophthalmia, cataracts, chorioretinal inflammation, focal chorioretinal inflammation, focal chorioretinitis, focal choroiditis, focal retinitis, focal retinochoroiditis, disseminated chorioretinal inflammation, disseminated chorioretinitis, disseminated choroiditis, disseminated retinitis, disseminated retinochoroiditis, exudative retinopathy, posterior cyclitis, pars planitis, Harada's disease, chorioretinal scars, macula scars of posterior pole, solar retinopathy, choroidal degeneration, choroidal atrophy, choroidal sclerosis, angioid streaks, hereditary choroidal dystrophy, choroideremia, choroidal dystrophy (central arealor), gyrate atrophy (choroid), ornithinaemia, choroidal haemorrhage and rupture, choroidal haemorrhage (not otherwise specified), choroidal haemorrhage (expulsive), choroidal detachment, retinoschisis, retinal artery occlusion, retinal vein occlusion, hypertensive retinopathy, diabetic retinopathy, retinopathy, retinopathy of prematurity, macular degeneration, Bull's Eye maculopathy, epiretinal membrane, peripheral retinal degeneration, hereditary retinal dystrophy, retinitis pigmentosa, retinal haemorrhage, separation of retinal layers, central serous retinopathy, retinal detachment, macular edema, glaucoma—optic neuropathy, glaucoma suspect—ocular hypertension, primary open-angle glaucoma, primary angle-closure glaucoma, floaters, Leber's hereditary optic neuropathy, optic disc drusen, strabismus, ophthalmoparesis, progressive external ophthaloplegia, esotropia, exotropia, disorders of refraction and accommodation, hypermetropia, myopia, astigmastism, anisometropia, presbyopia, internal ophthalmoplegia, amblyopia, Leber's congenital amaurosis, scotoma, anopsia, color blindness, achromatopsia, maskun, nyctalopia, blindness, River blindness, micropthalmia, coloboma, red eye, Argyll Robertson pupil, keratomycosis, xerophthalmia, aniridia, sickle cell retinopathy, ocular neovascularization, retinal neovascularization, subretinal neovascularization; rubeosis iritis inflammatory diseases, chronic posterior and pan uveitis, neoplasms, retinoblastoma, pseudoglioma, neovascular glaucoma; neovascularization resulting following a combined vitrectomy-2 and lensectomy, vascular diseases, retinal ischemia, choroidal vascular insufficiency, choroidal thrombosis, neovascularization of the optic nerve, diabetic macular edema, cystoid macular edema, proliferative vitreoretinopathy, and neovascularization due to penetration of the eye or ocular injury. In some embodiments, the ocular disease or disorder is selected from a group consisting of allergies, glaucoma, cataract, corneal disease, vitreo-retinal diseases, optic nerve diseases or disorders, oculosystemic diseases and disorders, uvea diseases or disorders, or diabetic eye disease. In some embodiments, the ocular disease or disorder is Meibomian gland inflammation or Meibomian gland dysfunction. In some embodiments, the ocular disease or disorder is dry eye disease.

Described herein, in some embodiments, are methods for administering to a subject with an ocular disease or disorder, wherein the daily dosage comprising fully hydrolyzed polyvinyl alcohol, partially hydrolyzed polyvinyl alcohol, and povidone is administered as one or more doses. In some embodiments, the fully hydrolyzed polyvinyl alcohol, partially hydrolyzed polyvinyl alcohol is administered as a plurality of doses, for example 1 2, 3, 4, 5, 6, 7, 8, 9, or 10 doses.

In some embodiments, one or more doses comprising fully hydrolyzed polyvinyl alcohol, partially hydrolyzed polyvinyl alcohol, and povidone is administered to the subject over a period of time. In some embodiments, the period of time is 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, or more than 12 weeks. The period of time, in some embodiments, is about 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, or more than 8 years. In some embodiments, the plurality of doses comprising fully hydrolyzed polyvinyl alcohol, partially hydrolyzed polyvinyl alcohol, and povidone is administered chronically. In some embodiments, one or more doses comprising fully hydrolyzed polyvinyl alcohol, partially hydrolyzed polyvinyl alcohol, and povidone is administered to the subject daily for a period of time.

Methods as described herein, in some embodiments comprise providing a dose of fully hydrolyzed polyvinyl alcohol, partially hydrolyzed polyvinyl alcohol, and povidone at least 1, 2, 3, 4, 5, 6, 7, 8, 9, 10, 11, 12 more than 12 times a day. In some embodiments, a dose of fully hydrolyzed polyvinyl alcohol, partially hydrolyzed polyvinyl alcohol, and povidone is administered at least 4 times a day. In some embodiments, a dose of fully hydrolyzed polyvinyl alcohol, partially hydrolyzed polyvinyl alcohol, and povidone is administered about once times a day. In some embodiments, a dose of fully hydrolyzed polyvinyl alcohol, partially hydrolyzed polyvinyl alcohol, and povidone is administered about 2 times a day. In some embodiments, a dose of fully hydrolyzed polyvinyl alcohol, partially hydrolyzed polyvinyl alcohol, and povidone is administered about 3 times a day. In some embodiments, a dose of fully hydrolyzed polyvinyl alcohol, partially hydrolyzed polyvinyl alcohol, and povidone is administered about 4 times a day. Administration, in some embodiments, is about every 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours. In some embodiments, a time between administration is at least or about 1 hour, 2 hours, 3 hours, 4 hours, 5 hours, 6 hours, 7 hours, 8 hours, 9 hours, 10 hours, 11 hours, 12 hours, or more than 12 hours. In some embodiments, a time between administration is in a range of 0 hours to 24 hours, 1 hour to 23 hours, 2 hours to 22 hours, 3 hours to 21 hours, 4 hours to 20 hours, 5 hours to 19 hours, 6 hours to 18 hours, 7 hours to 17 hours, 8 hours to 16 hours, 9 hours to 15 hours, and 10 hours to 12 hours.

In some embodiments, administration of formulations or compositions as described herein comprising fully hydrolyzed polyvinyl alcohol, partially hydrolyzed polyvinyl alcohol, and povidone to the subject results in improvements in symptoms associated with the ocular disease or disorder. In some embodiments, the administration of fully hydrolyzed polyvinyl alcohol, partially hydrolyzed polyvinyl alcohol, and povidone inhibits disease progression.

Administration of formulations or compositions described herein comprising fully hydrolyzed polyvinyl alcohol, partially hydrolyzed polyvinyl alcohol, and povidone, in some embodiments, results in an improvement in the ocular disease or disorder or symptoms of the ocular disease or disorder by at least 10% as compared to a control. In some embodiments, the improvement is by at least or about 10%, 15%, 20%, 25%, 30%, 35%, 40%, 45%, 50%, 60%, 70%, 80%, 90%, or more than 90% as compared to a control. In some embodiments, the improvement is an increase by at least or about 10%, 15%, 20%, 25%, 30%, 35%, 40%, 45%, 50%, 60%, 70%, 80%, 90%, or more than 90% as compared to a control. In some embodiments, the improvement is at least or about 0.5, 1.0, 1.5, 2.0, 2.5, 3.0, 3.5, 4.0, 4.5, 5.0, 6.0, 7.0, 8.0, or more than 8.0-fold as compared to a control. In some embodiments, the control is the subject at baseline, a subject administered placebo, a subject administered fully hydrolyzed polyvinyl alcohol, partially hydrolyzed polyvinyl alcohol, povidone, or combinations thereof.

Kits/Article of Manufacture

Disclosed herein, in certain embodiments, are kits and articles of manufacture for use with one or more methods, compositions, and formulations described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include one or more compositions or formulations comprising fully hydrolyzed polyvinyl alcohol, partially hydrolyzed polyvinyl alcohol, and optionally one or more pharmaceutical excipients described herein to facilitate the delivery of fully hydrolyzed polyvinyl alcohol, partially hydrolyzed polyvinyl alcohol. Such kits further optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself, a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the compositions or formulations are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for drugs, or the approved product insert. In one embodiment, compositions containing a compound provided herein formulated in a compatible pharmaceutical carrier are also prepared, placed in an appropriate container, and labeled for treatment of an indicated condition.

Dropper Bottle or Storage Bottle

In some embodiments, formulations and compositions as described herein are administered using a dropper bottle. In some embodiments, the dropper bottle comprises a squeezable container is provided with a tapered dispenser that terminates in a discharge aperture. In some embodiments, to administer ophthalmic fluid, the discharge aperture is aligned above a target eye and the bottle is squeezed to urge out a drop or dose of the fluid.

Alternatively, liquid dispensers have been developed in which the formulation is supplied from a storage bottle through a dropper, for example (dropper bottles or EDO- Ophthiols). The aqueous formulation, in some embodiments, flows out of the dropper opening as a result of manual pressure being applied to the compressible storage bottle.

In some embodiments, the formulations and compositions described herein are stored in a plastic or glass bottle. In some embodiments, the plastic bottle is a low-density polyethylene bottle. In some embodiments, the composition described herein is stored in a glass bottle with or without a liquid dispenser. In some embodiments, the plastic or glass bottle is opaque.

In some embodiments, the formulations and compositions described herein are provided in a 5, 7.5, 10, 15, 20, 25, or 30 mL bottle. In some embodiments the formulations and compositions described herein are provided in a 15 mL bottle.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Exemplary Formulations

TABLE 1

Exemplary Formulation 1

| Component | Concentration (mg/mL) | Concentration (% w/w) |
| --- | --- | --- |
| Povidone K-29-32, USP | 10.0-30.0 mg/mL | 1.00-3.00% |
| Polyvinyl Alcohol (Fully Hydrolyzed), Grade BF04 | 10.0-30.0 mg/mL | 1.00-3.00% |
| Polyvinyl Alcohol (87% Hydrolyzed), Grade BF05 | 1.0-15.0 mg/mL | 0.10-1.50% |
| Sodium Chloride, USP | 1.0-10.0 mg/mL | 0.10-1.00% |
| Boric Acid, NF | 1.0-10.0 mg/mL | 0.10-1.00% |
| Disodium Edetate, Dihydrate, USP | 1.0-10.0 mg/mL | 0.10-1.00% |
| Potassium Chloride, USP | 0.05-4 mg/mL | 0.005-0.4% |
| Amisol Clear | 0.01-4 mg/mL | 0.001-0.4% |
| 1N Sodium Hydroxide, NF 1N Hydrochloric Acid NF | To adjust pH to 6.6 to 6.9 | |
| Water for injection, USP | Dilute to Volume to make 1 mL | Dilute to final weight |
| Final Product pH Target | pH 6.6-6.9 | |
| Final Product Osmolality | 260-330 mOsm/kg | |
| Specific Gravity | TBD | |

TABLE 2

Exemplary Formulation 2

| Ingredient | Reference to Quality Standard | Concentration (% w/v) | Amount per Batch Batch Size: 400 L |
| --- | --- | --- | --- |
| Povidone K30* | USP-NF | 1.00-3.00% | 1-20 kg* |
| Polyvinyl Alcohol (28-99)* | EP | 0.10-1.50% | 1-10 kg* |
| Polyvinyl Alcohol (5-88)* | USP | 1.00-3.00% | 1-10 kg* |
| Sodium Chloride | USP-NF | 0.10-1.50% | 0.5-10 kg |
| Boric Acid, USP | USP-NF | 0.10-1.50% | 0.1-8 kg |
| Disodium Edetate, Dihydrate | USP-NF | 0.010-1.50% | 0.1-8 kg |
| Potassium Chloride | USP-NF | 0.010-1.50% | 0.1-8 kg |
| Glycerin | USP-NF | 0.0010-1.00% | 0.01-4 kg |
| Ethyl Alcohol 96% | EP | 0.0010-1.00% | 0.001-2 kg |
| Lecithin | USP-NF | 0.0010-1.00% | 0.001-2 kg |
| Polysorbate 80 | USP-NF | 0.0010-1.00% | 0.01-4 kg |
| Sodium Hydroxide 1N Solution or Hydrochloric acid 1N | USP | adjust Povidone phase to pH 6.35 ± 0.05 | QS |
| Water for Injection | USP | QS to 100% | QS to 400.0 L |

*The exact quantity of RM to weight will take into account the % of water of the API Example 2: Methods for Manufacturing Exemplary Formulation 1

Compounding
PVA Phase Preparation

The PVA Phase was prepared by dispersing the Polyvinyl Alcohol 5-88 and Polyvinyl Alcohol 28-99 in cold water using amounts as seen in Table 3 and Table 4. Following dispersion, the dispersed PVA suspension was heated to 95°-100° C. to dissolve the PVA. Following dissolution, the pH of the PVA phase was determined. The initial pH of the PVA phases ranged from pH 5.3 to pH 5.6. The pH of the PVA phase was then adjusted to pH 6.5 to 6.9 with 0.5 N Sodium Hydroxide. The final pH of the PVA phased ranged from pH 6.9 to pH 8.9. Since the PVA phase is not buffered, small additions of sodium hydroxide resulted in large changes in pH. During the pH adjustment, most samples were outside the range of 6.5 to 6.9 (Table 3 and Table 4).

As this was the result of very small quantities of sodium hydroxide (one drop), re-adjusting with acid was not necessary. Additionally, when the PVA phase was combined with the PVP/excipient phase, the resulting pH was below the pH of the two phases (Table 5 and Table 6). For the Cold Process and No Boric Acid, the PVA phase was allowed to cool to room temperature prior to pH adjustment. For all other processes, the pH of the PVA phase was adjusted while hot.

TABLE 3

PVA Phase Critical Parameters for Lots EPS772-082, -083, and -084 (1.0 L Batches)

| Component/ Parameter | Target (Range) | Cold Process EPS772-082 | No Boric Acid EPS772-083 | Hot Process EPS772-084 |
|---|---|---|---|---|
| Polyvinyl Alcohol 5-88 | 5-15 g | 5-15 g | 5-15 g | 5-15 g |
| Polyvinyl Alcohol 28-99 | 15-25 g | 15-25 g | 15-25 g | 15-25 g |
| Initial pH | pH 6.6-6.9 | 5.337 | 5.377 | 5.530 |
| Final pH | | 7.974 | 8.927 | 8.670 |

Polyvinyl alcohol weights corrected for water content: PVA 5-88-1.1%; PVA 28-99-1.4%

TABLE 4

PVA Phase Critical Parameters for Lots EPS772-101 and -103 (2.0 L Batches)

| Component/ Parameter | Target (Range) | Hot Process No Homogenization EPS772-101 | Hot Process Homogenization EPS772-103 |
|---|---|---|---|
| Polyvinyl Alcohol 5-88 | 15-25 g | 15-25 g | 15-25 g |
| Polyvinyl Alcohol 28-99 | 30-40 g | 30-40 g | 30-40 g |
| Initial pH | pH 6.6-6.9 | 5.538 | 5.651 |
| Final pH | | 6.940 | 7.080 |

Polyvinyl alcohol weights corrected for water content.. PVA 5-88-1.1%; PVA 28-99-1.4%

For Lot EPS772-103, the hot PVA solution was homogenized at 20,000 rpm for 20 minutes using the Polytron PT 10-35 homogenizer following the pH adjustment. Due to the volume of the PVA solution and the configuration of the homogenizer, a considerable quantity of PVA foam was generated during the process. Prior to use, the foam was allowed to dissipate.

Povidone/Excipient Phase

The Povidone/Excipient phases were prepared by adding and completely dissolving each component using the following order of addition: sodium chloride, USP; potassium chloride; boric acid, NF; edetate disodium, dihydrate, USP; and povidone K-30, USP. For the Cold Process and No Boric Acid, the Amisol Clear was added following the dissolution of the povidone. For the Hot Process Batches, EPS772-084, -101, and -103, the Amisol Clear was added following the combination of the two phases after the solution had cooled to room temperature. The quantities of povidone and excipients used in each batch and the critical process parameters are summarized in Table 5 and Table 6.

TABLE 5

Povidone/Excipient Phase Critical Parameters for Lot EPS772-082, -083, and -084 (1.0 L Batches)

| Component/ Parameter | Target (Range) | Cold Process EPS772-082 | No Boric Acid EPS772-083 | Hot Process EPS772-084 |
|---|---|---|---|---|
| Sodium Chloride, USP | 1-10 g | 1-10 g | 1-10 g | 1-10 g |
| Potassium Chloride | 0.5-4 g | 0.5-4 g | 0.5-4 g 0.5-4 g | |
| Boric Acid, NF | 1-10 g | 1-10 g | N/A | 1-10 g |
| Edetate Disodium, Dihydrate, USP | 0.05-5 g | 0.05-5 g | 0.05-5 g | 0.05-5 g |
| Povidone K-30, USP | 15-30 g | 15-30 g | 15-30 g | 15-30 g |
| Amisol Clear | 0.1-2 g | 0.1-2 g | 0.1-2 g | 0.1-2 g |
| Initial pH | pH 6.6-6.9 | 3.836 | 3.838 | 3.925 |
| Final pH | | 6.848 | 6.789 | 6.802 |

Povidone weight corrected for water content: 3.2%

TABLE 6

Povidone/Excipient Phase Critical Parameters for Lot EPS772-101 and -103 (2.0 L Batches)

| Component/ Parameter | Target (Range) | Hot Process No Homogenization EPS772-101 | Hot Process Homogenization EPS772-103 |
|---|---|---|---|
| Sodium Chloride, USP | 5-15 g | 5-15 g | 5-15 g |
| Potassium Chloride | 0.5-5 g | 0.5-5 g | 0.5-5 g |
| Boric Acid, NF | 1-10 g | 1-10 g 1-10 g | |
| Edetate Disodium, Dihydrate, USP | 1-10 g | 1-10 g 1-10 g | |
| Povidone K-30, USP 2FL0288 | 30-50 g | 30-50 g | |
| Povidone K-30, USP 2GC0405 | 30-50 g | | 30-50 g |
| Amisol Clear | 0.5-5 g | 0.5-5 g 0.5-5 g | |
| Initial pH | pH 6.6-6.9 | 3.877 | 3.752 |
| Final pH | | 6.930 | 6.931 |

Povidone weight corrected for water content: Lot 2FL0288-3.2%; Lot 2GC0405-2.7%

Phase Combination and Final QS

Following the pH adjustment of the PVA and Povidone/Excipient Phases, the phases were combined by adding the PVA solution to the Povidone/Excipient Phase while stirring. For the Hot Process batches, the solutions were allowed to cool to room temperature; then the Amisol Clear was added. All solutions were brought to final weight with the addition of water (Target weight: 1.0 L=1048 g; 2.0 L=2096 g). The final batch weights and in-process bulk pHs are listed in Table 7 and Table 8. The pH specification for the cold process manufacturer was 6.6 to 6.9. The pH specification for the hot process manufacturer was 6.0 to 7.0. For these lots, the pH was not adjusted after mixing the two phases.

TABLE 7

Final Batch Weight and Bulk pH for 1.0 L Batches

| Parameter | Target (Range) | Cold Process EPS772-082 | No Boric Acid EPS772-083 | Hot Process EPS772-084 |
|---|---|---|---|---|
| Final Batch Weight | 950-1200 g | 950-1200 g | 950-1200 g | 950-1200 g |
| Final pH | pH 6.6-6.9 | 6.461 | 6.845 | 6.393 |

TABLE 8

Final Batch Weight and Bulk pH for 2.0 L Batches

| Parameter | Target (Range) | Hot Process No Homogenization EPS772-101 | Hot Process Homogenization EPS772-103 |
|---|---|---|---|
| Final Batch Weight | 1500-2500 g | 1500-2500 g | 1500-2500 g |
| Final pH | pH 6.6-6.9 | 6.478 | 6.472 |

Filtration

The filtration study was performed using a standard pressure set-up. Approximately 1.0 L of Exemplary Formulation 1 was added to a 20 L Millipore Stainless Steel Pressure Can. The pressure can was attached to a cylinder of Ultra Pure Nitrogen and connected to the filter train via Cole Parmer L/S 24 Platinum Cured Silicone Tubing. Two filter trains were utilized for these studies: (1) the Millipore OptiScale 47 Polysep™ II 2.0/1.2 um Nominal Pre-Filter in series with a Millipore Durapore 47 mm 0.2 um sterilizing filter or (2) the Millipore Durapore 47 mm 0.2 um sterilizing filter alone. The Pre-filter was attached to the sterilizing filter housing via a short length of L/S 24 Platinum Cured Silicone tubing.

Filtration studies were initiated by applying approximately 30 psig nitrogen to the system. Flow through the filter was determined gravimetrically and recorded every minute. Flow-Decay curves were prepared by plotting the amount of Exemplary Formulation 1 flowing through the filter per minute.

Analytical Testing

Pre- and post-filtration samples of Exemplary Formulation 1 were submitted for analytical evaluation (Table 9).

TABLE 9

Pre- and Post-Filtration Testing Method

Appearance
pH
Osmolality
Viscosity
Surface Tension
Potency-Povidone
Potency-Polyvinyl Alcohol Results Cold Process—EPS772-082

Filtration was performed under a constant pressure of 25 psig (1.2 Bar) using DURAPORE® Membrane Filters, 0.22 um GV (Millipore). The initial flow rate was 9.2 g/minute (FIG. 1). The flow rate decreased to 0.3 g/minute at 1 hour and 50 minutes. A total of 258.22 g of Cold Processed Exemplary Formulation 1 was filtered. Scaling these results to a 10 inch filter cartridge, the Cold process using a PVDF filter would allow approximately 129 L to be filtered with a final flow rate of 150 mL/min.

FIG. 1 indicates a significant reduction in filtration flow rate over time. A comparison of pre- and post-filtration results (Table 10) indicates that the flow rate reduction is not due to substantial filter binding of the actives (polyvinyl alcohol and povidone). Pre- and post-filtration analytical test results indicated that there was not a significant change to the composition or physical properties of Exemplary Formulation 1 due to filtration.

TABLE 10

Cold-Process Pre- and Post-Filtration Test Results

| Test | Pre-Filtration | Post-Filtration |
|---|---|---|
| Appearance | Clear, colorless solution, free of visible particles | Clear, colorless solution, free of visible particles |
| pH | 6.5 | 6.5 |
| Osmolality | 268 mOsm/kg | 288 mOsm/kg |
| Viscosity | 8.86 cps at 25° C. | 9.21 cps at 25° C. |
| Surface Tension | 49.6 dynes/cm | 49.9 dynes/cm |
| Potency-Povidone | 94.4% | 97.1% |
| Potency-Polyvinyl Alcohol | 121.7% | 127.0% |

No Boric Acid—EPS772-083

Compounding of the No Boric Acid Process batch was completed and the filtration study was performed using DURAPORE® Membrane Filters, 0.22 um GV (Millipore). Although this sample was filtered 10 days after preparation, the samples remained clear and did not exhibit signs of contamination. In a previous study, three month old un-filtered samples of this formulation had a bioburden of <10 cfu/mL.

Figure 2:
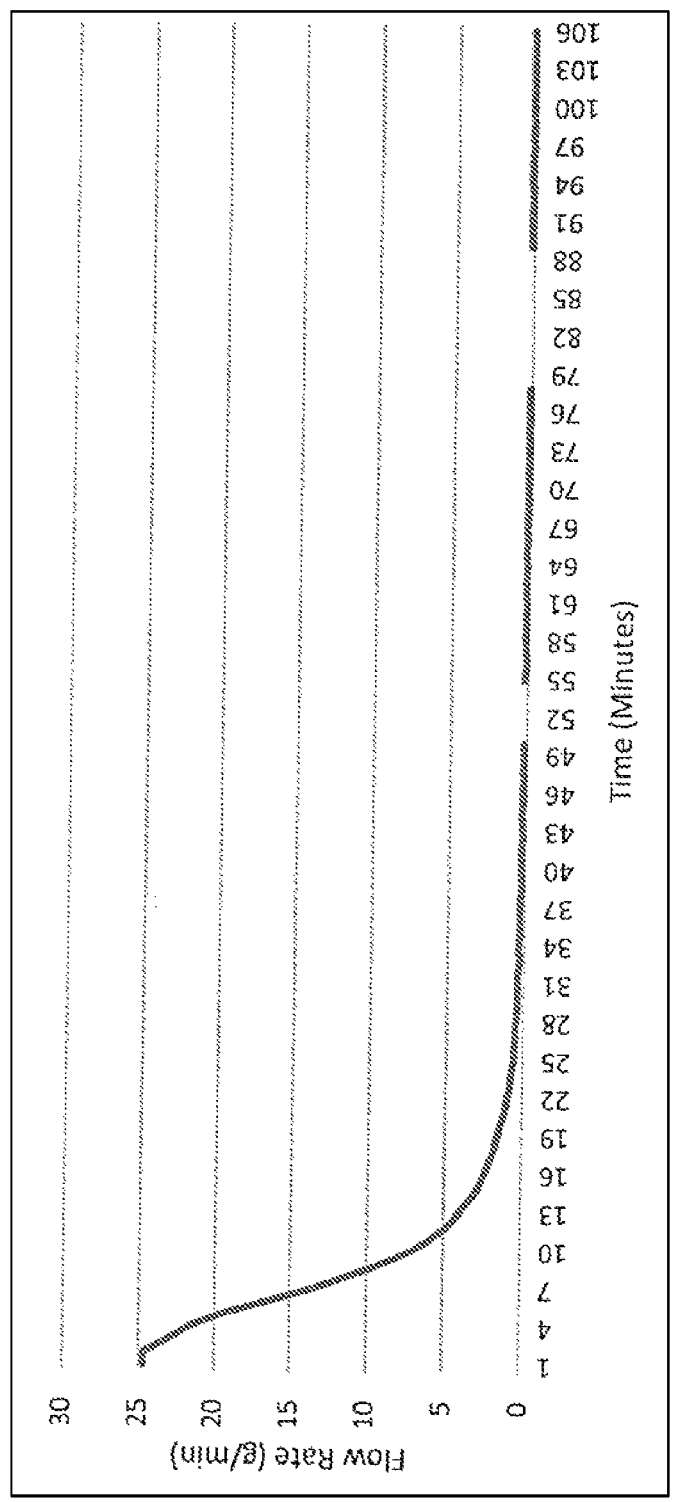
FIG. 2 is a graph of filtration flow rate for Exemplary Formulation 1 without boric acid. The x-axis is time (minutes) and the y-axis is flow rate (g/min.).

Filtration was performed under a constant pressure of 30 psig. The initial flow rate was 22.90 g/minute (FIG. 2). The flow rate decreased to 0.13 g/minute at 106 minutes. A total of 225.66 g of No Boric Acid Processed Exemplary Formulation 1 was filtered. Scaling these results to a 10 inch filter cartridge, the No Boric Acid process using a PVDF filter would allow approximately 113 L to be filtered with a final flow rate of 65 mL/min.

FIG. 2 indicates a significant reduction in filtration flow rate over time. A comparison of pre- and post-filtration results (Table 11) indicates that the flow rate reduction is not due to substantial filter binding of the actives (polyvinyl alcohol and povidone). Pre- and post-filtration analytical test results indicated that there was not a significant change to the composition or physical properties of Exemplary Formulation 1 due to filtration.

TABLE 11

No Boric Acid Pre- and Post-Filtration Test Results

| Test | Pre-Filtration | Post-Filtration |
|---|---|---|
| Appearance | Clear, colorless solution, free of visible particles | Clear, colorless solution, free of visible particles |
| pH | 6.8 | 6.7 |
| Osmolality | 247 mOsm/kg | 249 mOsm/kg |
| Viscosity | 8.56 cps at 25° C. | 7.56 cps at 25° C. |
| Surface Tension | 48.5 dynes/cm | 48.1 dynes/cm |
| Potency-Povidone | 96.7% | 96.6% |
| Potency-Polyvinyl Alcohol | 124.8%* | 127.8%* |

*PVA assay biased high due to use of low molecular weight standard

Hot Process—EPS772-084

Compounding of the Hot Process batch was completed and the filtration study was performed using DURAPORE® Membrane Filters, 0.22 um GV (Millipore).

Figure 3:
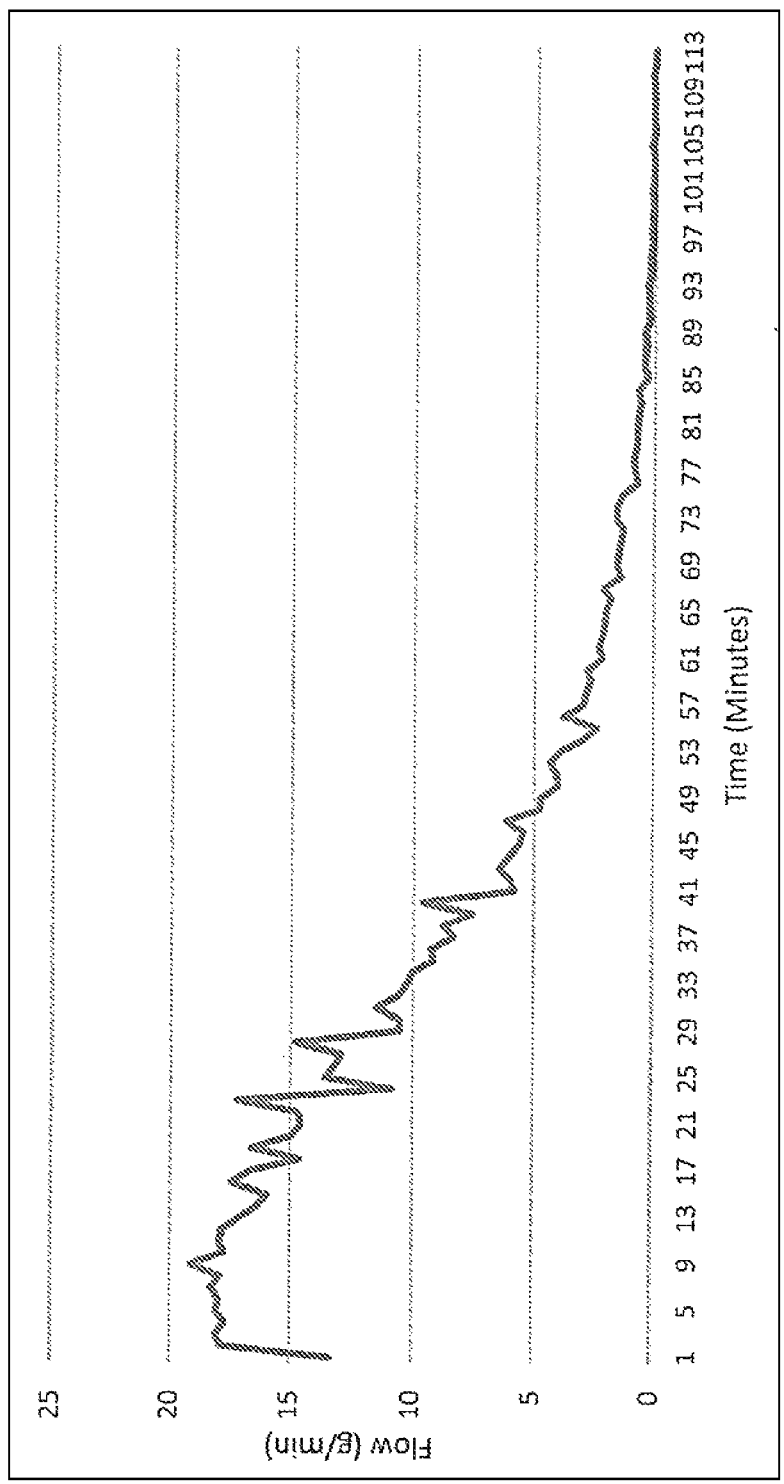
FIG. 3 is a graph of filtration flow rate for Exemplary Formulation 1 using the Hot Process. The x-axis is time (minutes) and the y-axis is flow rate (g/min.).

Filtration was performed under a constant pressure of 30 psig. The initial flow rate was 13.40 g/minute (FIG. 3). The flow rate decreased to 0.08 g/minute at 113 minutes. A total of 701.51 g of Hot Processed Exemplary Formulation 1 was filtered. Scaling these results to a 10 inch filter cartridge, the Hot Process using a PVDF filter would allow approximately 351 L to be filtered with a final flow rate of 40 mL/min.

FIG. 3 indicates a significant reduction in filtration flow rate over time. A comparison of pre- and post-filtration results (Table 12) indicates that the flow rate reduction is not due to substantial filter binding of the actives (polyvinyl alcohol and povidone). Pre- and post-filtration analytical test results indicated that there was not a significant change to the composition or physical properties of Exemplary Formulation 1 due to filtration.

flow rate decreased to 6.68 g/minute at 119 minutes. A total of 952.51 g of Hot Processed Exemplary Formulation 1 was filtered. Scaling these results to a 10 inch filter cartridge, the Hot Process/Pre-Filter process using a PVDF filter would allow approximately 477 L to be filtered with a final flow rate of 3.34 L/min.

Figure 4:
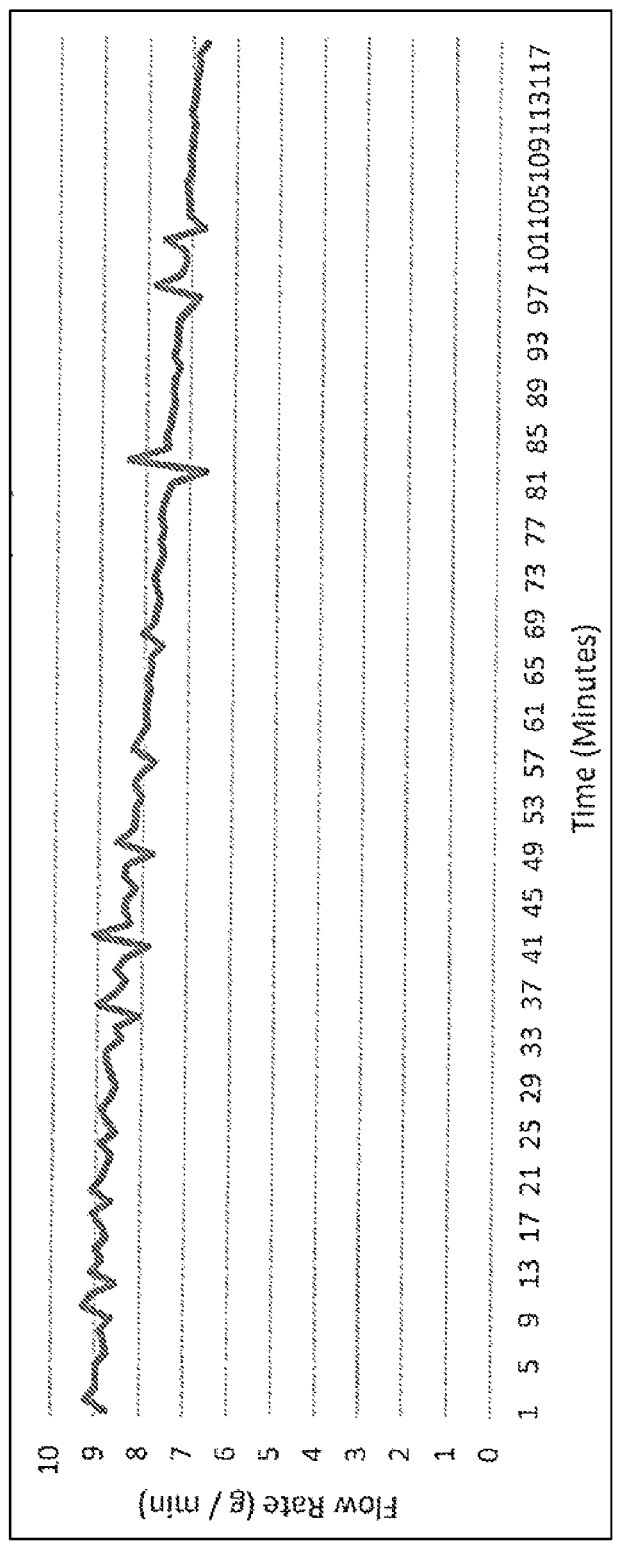
FIG. 4 is a graph of filtration flow rate for Exemplary Formulation 1 using the Hot Process and pre-filtration. The x-axis is time (minutes) and the y-axis is flow rate (g/min.).

FIG. 4 indicates a slight reduction in filtration flow rate over time. A comparison of pre- and post-filtration results (Table 13) indicates that the flow rate reduction is not due to substantial filter binding of the actives (polyvinyl alcohol and povidone). Pre- and post-filtration analytical test results indicated that there was not a significant change to the composition or physical properties of Exemplary Formulation 1 due to filtration.

TABLE 13

Hot Process/Pre-Filter-Pre- and Post-Filtration Test Results

| Test | Pre-Filtration | Post-Filtration |
| --- | --- | --- |
| Appearance | Clear, colorless solution, free of visible particles | Clear, colorless solution, free of visible particles |
| PH | 6.5 | 6.5 |
| Osmolality | 275 mOsm/kg | 272 mOsm/kg |
| Viscosity | 8.52 cps at 25° C. | 8.37 cps at 25° C. |
| Surface Tension | 46.9 dynes/cm | 49.8 dynes/cm |
| Potency-Povidone | 102.0% | 104.5% |
| Potency-Polyvinyl Alcohol Low Molecular Weight STD | 125.8% | 124.3% |
| Potency-Polyvinyl Alcohol High Molecular Weight STD | 99.2% | 100.3% |

TABLE 12

Hot Process Pre- and Post-Filtration Test Results

| Test | Pre-Filtration | Post-Filtration |
| --- | --- | --- |
| Appearance | Clear, colorless solution, free of visible particles | Clear, colorless solution, free of visible particles |
| pH | 6.4 | 6.4 |
| Osmolality | 271 mOsm/kg | 281 mOsm/kg |
| Viscosity | 8.80 cps at 25° C. | 9.54 cps at 25° C. |
| Surface Tension | 48.7 dynes/cm | 48.7 dynes/cm |
| Potency-Povidone | 97.5% | 97.1% |
| Potency-Polyvinyl Alcohol | 124.9%* | 125.8%* |

*PVA assay biased high due to use of low molecular weight standard

Hot Process/No Homogenization—EPS772-101

Compounding of the Hot Process batch was completed and the filtration study was performed using DURAPORE® Membrane Filters, 0.22 um GV (Millipore) or OptiScale®47 Capsule Media: Polysep™ II 2.0/1.2 um Nominal (Millipore).

Filtration was performed under a constant pressure of 30 psig. The initial flow rate was 8.79 g/minute (FIG. 4). The Hot Process/Homogenization/No Pre-Filter—EPS772-103

Compounding and homogenization of the Hot Process batch was completed and the no pre-filter filtration study was performed using DURAPORE® Membrane Filters, 0.22 um GV (Millipore).

Figure 5:
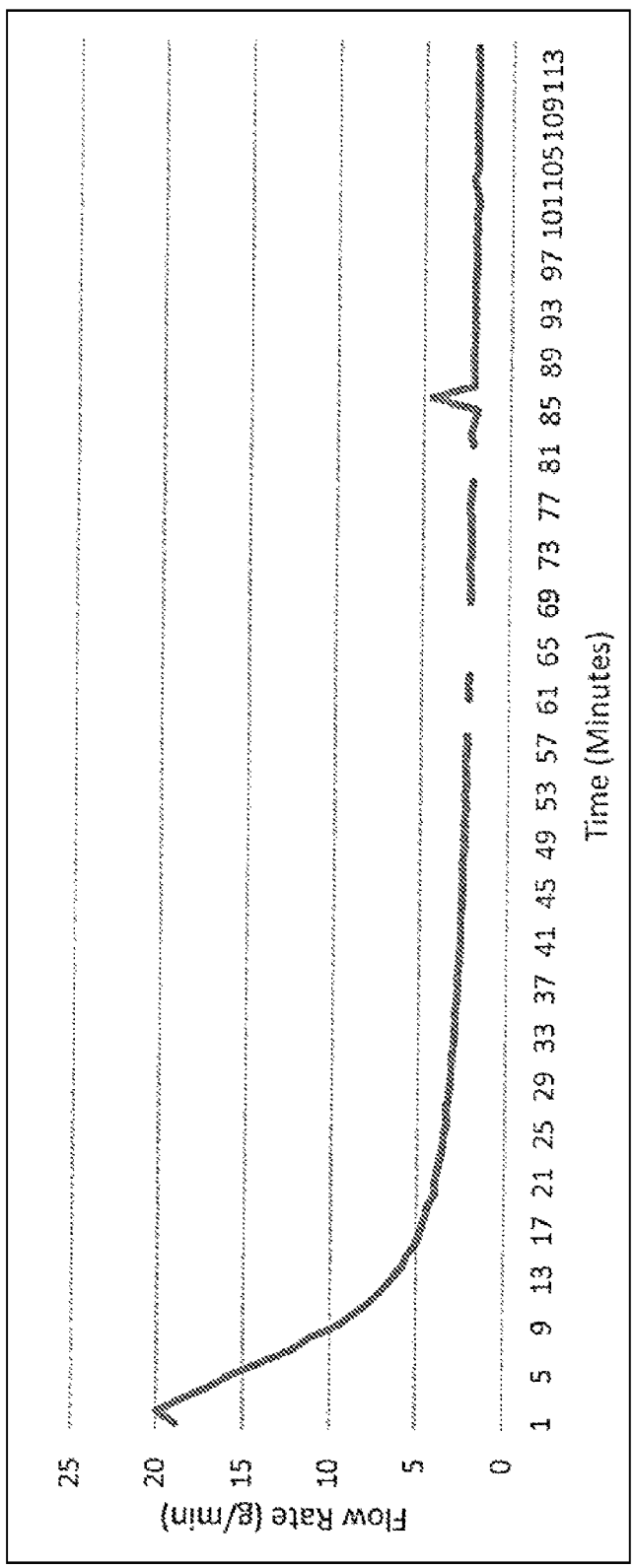
FIG. 5 is a graph of filtration flow rate for Exemplary Formulation 1 using the Hot Process and homogenization. The x-axis is time (minutes) and the y-axis is flow rate (g/min.).

Filtration was performed under a constant pressure of 30 psig. The initial flow rate was 19.01 g/minute (FIG. 5). The flow rate decreased to 2.05 g/minute at 115 minutes. A total of 437.89 g of Hot Homogenized Processed Exemplary Formulation 1 was filtered. Scaling these results to a 10 inch filter cartridge, the Hot Process/Pre-Filter process using a PVDF filter would allow approximately 219 L to be filtered with a final flow rate of 1.025 L/min.

FIG. 5 indicates a significant reduction in filtration flow rate over time. A comparison of pre- and post-filtration results (Table 14) indicates that the flow rate reduction is not due to substantial filter binding of the actives (polyvinyl alcohol and povidone). Pre- and post-filtration analytical test results indicated that there was not a significant change to the composition or physical properties of Exemplary Formulation 1 due to filtration. Homogenization did not appear to affect viscosity but resulted in an approximate 8% drop in measured PVA.

TABLE 14

Hot/Homogenized Process Pre- and Post-Filtration Test Results

| Tests | Pre-Filtration | Post-Filtration |
| --- | --- | --- |
| Appearance | Clear, colorless solution, free of visible particles | Clear, colorless solution, free of visible particles |
| PH | 6.5 | 6.5 |
| Osmolality | 278 mOsm/kg | 279 mOsm/kg |

TABLE 14-continued

Hot/Homogenized Process Pre- and Post-Filtration Test Results

| Tests | Pre-Filtration | Post-Filtration |
|---|---|---|
| Viscosity | 8.32 cps at 25° C. | 9.19 cps at 25° C. |
| Surface Tension | 49.5 dynes/cm | 48.7 dynes/cm |
| Potency-Povidone | 102.6% | 99.8% |
| Potency-Polyvinyl Alcohol Low Molecular Weight STD | 117.8% | 113.5% |
| Potency-Polyvinyl Alcohol High Molecular Weight STD | 92.9% | 90.5% |

Hot Process/Homogenization/Pre-Filter—EPS791-003

Compounding and homogenization of the Hot Process batch (EPS772-103) was completed and the pre-filter filtration study was performed using DURAPORE® Membrane Filters, 0.22 um GV (Millipore) or OptiScale®47 Capsule Media: Polysep™ II 2.0/1.2 um Nominal (Millipore).

Figure 6:
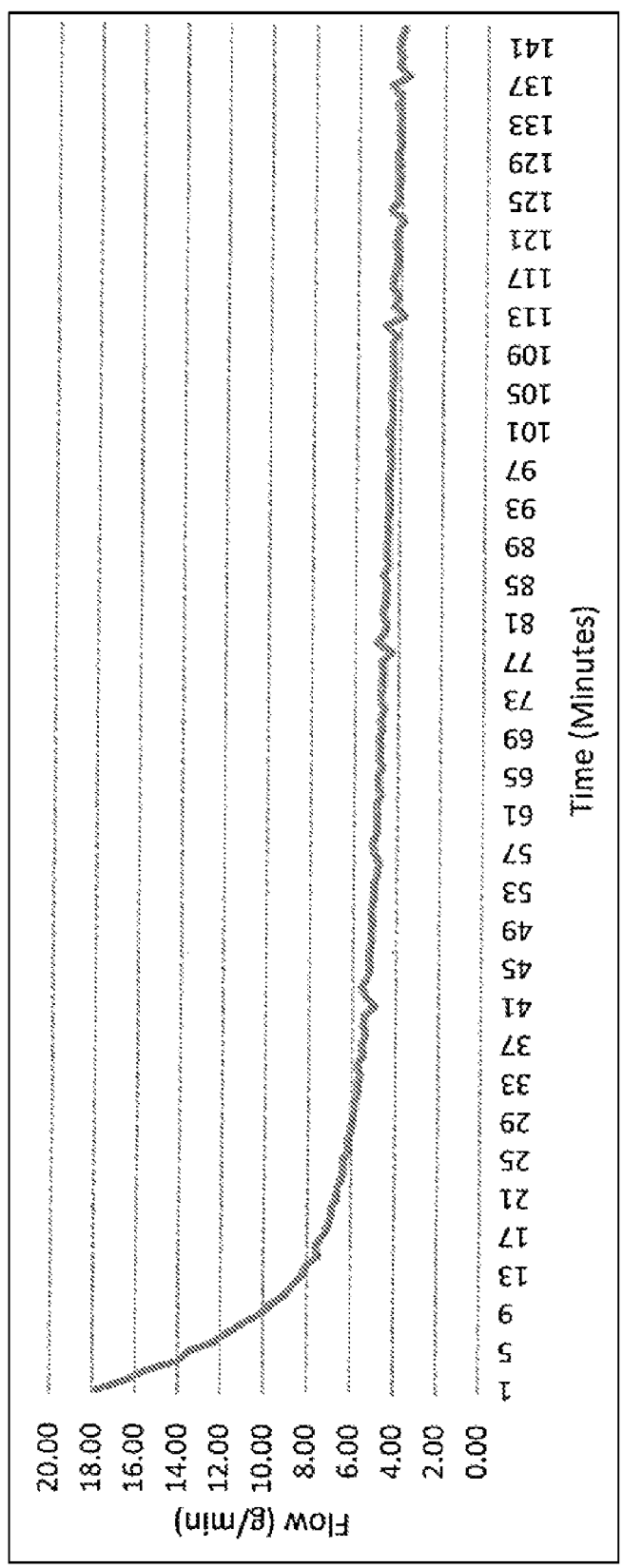
FIG. 6 is a graph of filtration flow rate for Exemplary Formulation 1 using the Hot Process with 2.0 and 1.2 um pre-filter. The x-axis is time (minutes) and the y-axis is flow rate (g/min.).

Filtration was performed under a constant pressure of 30 psig. The initial flow rate was 17.84 g/minute (FIG. 6). The flow rate decreased to 3.95 g/minute at 144 minutes. A total of 819.99 g of Hot Homogenized Processed Exemplary Formulation 1 was filtered. Scaling these results to a 10 inch filter cartridge, the Hot Process/Pre-Filter process using a PVDF filter would allow approximately 410 L to be filtered with a final flow rate of 1.975 L/min.

FIG. 6 indicates a significant reduction in filtration flow rate over time. A comparison of pre- and post-filtration results (Table 15) indicates that the flow rate reduction is not due to substantial filter binding of the actives (polyvinyl alcohol and povidone). Pre- and post-filtration analytical test results indicated that there was not a significant change to the composition or physical properties of Exemplary Formulation 1 due to filtration.

Pre-filtration of homogenization material resulted in a slight decrease in viscosity and measured PVA as compared to the batch which did not use the pre-filter (EPS772-103B—Table 14).

the processes or between the pre- and post-filtration analytical testing results.

At the beginning of this study, a low molecular weight 99% hydrolyzed polyvinyl alcohol standard was used for the analytical potency tests. Since the drug product samples used in this study were prepared with high molecular weight 99% hydrolyzed polyvinyl alcohol, the use of this low molecular weight standard yielded potency results with a 20 to 25% bias (Table 10, Table 11, and Table 12). Samples tested at the end of this study used an analytical standard prepared with the same high molecular weight 99% hydrolyzed polyvinyl alcohol used to prepare the drug product samples. Use of the high molecular weight standard yielded results closely matching the target values for polyvinyl alcohol in the sample (Table 13, Table 14, and Table 15). These results indicate that the unexpectedly high PVA potency results reported in Table 10, Table 11, and Table 12 were due to the use of the incorrect analytical standard and not due to incorrect sample preparation.

Homogenization of the hot polyvinyl alcohol phase resulted in an 8 to 10% loss in polyvinyl alcohol for both the pre- and post-filtration samples (Table 14 and Table 15, compared to Table 13). There was also slight decrease in viscosity noted in the hot homogenized polyvinyl alcohol product which was pre-filtered.

TABLE 15

Hot/Homogenized Process Pre- and Post-Filtration Test Results

| Tests | Pre-Filtration | Post-Filtration |
|---|---|---|
| Appearance | Clear, colorless solution, free of visible particles | Clear, colorless solution, free of visible particles |
| PH | 6.5 | 6.5 |
| Osmolality | 275 mOsm/kg | 279 mOsm/kg |
| Viscosity | 7.70 cps at 25° C. | 7.88 cps at 25° C. |
| Surface Tension | 49.2 dynes/cm | 48.9 dynes/cm |
| Potency-Povidone | 98.5% | 100.4% |
| Potency-Polyvinyl Alcohol Low Molecular Weight STD | 112.8% | 114.9% |
| Potency-Polyvinyl Alcohol High Molecular Weight STD | 88.6% | 88.9% |

Summary

This Example outlines the studies performed to understand the variables affecting the viscosity and filterability of Exemplary Formulation 1. Six different processes were investigated (cold, no boric acid, hot, hot pre-filtered, hot homogenized, and hot homogenized pre-filtered).

For the non-homogenized processes (cold, no boric acid, and hot pre-filtered), no significant differences in any parameters including viscosity, filterability, or product attributes such as pH, osmolality, or potency were observed between Sterile filtration (0.2 um) of the Exemplary Formulation 1 products produced by any of the processes evaluated resulted in a rapid loss of filter throughput regardless of the process. The hot process resulted in a more efficient filtration than the cold and no boric acid processes.

Use of an OptiScale 47 Polysep II 2.0/1.2 um Nominal pre-filter with the hot process improved the filtration allowing 952.51 g Exemplary Formulation 1 to be filtered at a flow rate of 6.79-8.79 g/minutes. Scaling these results to a 10 inch filter cartridge, the Hot Process/Pre-Filter process using a PVDF filter would allow approximately 477 L to be filtered with a final flow rate of 3.34 L/min.

Example 3: Methods for Manufacturing Exemplary Formulation 2

Compounding

Compounding of Solution A

Polyvinyl alcohol (5-88) and polyvinyl alcohol (28-99) as seen in Table 2 were introduced into a double jacket stainless steel tank, equipped with agitator, 192 kg of water for injection at ≥75° C. Polyvinyl alcohol (5-88) and polyvinyl alcohol (28-99) were introduced very slowly while stirring. The solution was heated to 92.5±2.5° C. Once the temperature was reached, the solution was homogenized under stirring for at least 30 minutes, until complete dissolution of polyvinyl alcohol (PVA). The solution temperature was maintained in the range 80-95° C.

Compounding of Solution C

In a 0.75 L beaker, glycerin, ethyl alcohol, lecithin, polysorbate 80, and WFI (about 200 g) were introduced successively and slowly under stirring. The reagents were dissolved under stirring for a minimum of 1 hour.

Compounding of Solution B

In a double jacket stainless steel tank equipped with agitator, about 192 kg of water was introduced for injection at ≥75° C. The tank was cooled down to 20-25° C. 2 kg from the tank was withdrawn and kept in a beaker to rinse the raw material containers after introduction of solution C. 5 kg from the tank was withdrawn and kept in a beaker for QS after pH adjustment. Sodium chloride, potassium chloride, boric acid, disodium edetate dehydrate, and povidone K30 were introduced and dissolved successively while stirring. The solution was homogenized while stirring for minimum 20 minutes. The pH was measured of the solution and adjusted if necessary under stirring with the solution of NaOH 1N in order to obtain a pH of 6.35±0.05. The solution continued to be homogenized while stirring for at least 10 minutes, and the pH was remeasured. The solution was then heated to 80-95° C. Once the temperature was reached, Solution A was checked to determine if the temperature was maintained between 80° C. and 95° C. Solution A was then transferred to Solution B. The tank containing Solution A was rinsed with the 5 kg of water set aside for that purpose. After the transfer, the tank was cooled to 20-25° C. while stirring. Solution C was then introduced and dissolved while stirring. The container was rinsed with the 2 kg of water set aside for that purpose. After the last addition, the solution was mixed for at least 10 minutes. Water for injection was used for any weight adjustment for QS 400 L if needed. The pH was measured to be in a range of 6.3-6.5. Samples of the solution were also taken for bioburden and analytical testing.

Filtration, Aseptic Storage of Solution and Filling Operation

The compounded solution was then transferred to the sterile storage tank through 2 successive filters under sterile nitrogen or air pressure (differential pressure of max 2.0 bar): 1.2 µm cellulose ester prefilter (Millipore) and sterile PVDF filter 0.2 µm (Pall). Between the 2 filters, in process samples were taken for bioburden. The solution was maintained with moderate stirring. The solution stored in the storage tank was then pushed to the sterilized blow-fill-seal machine R24. The filling was performed into natural LDPE single dose units and the volume for the unidose is set in order to deliver a volume of 0.3 mL minimum. At the beginning of the filling operations, a drain of the filling circuit was planned: it was defined as first 600 cards of 5 single dose units (at least) which were discarded. The osmolality on the first manufactured doses after drain was evaluated (5.3). During the filling step In-Process samples and extra samples were taken for analytical and microbiological testing.

Leak Detecting and Labelling

For leak detection, each block of 5 vials was tested in a vacuum chamber (Wilco). 100% of the batch was tested. A label was put on each vial in-line with the filling.

Secondary Packaging

Batch number and expiry date were jet printed on the pouch during the packaging

Critical Process Parameters

The critical process parameters are shown in the Tables 16-20 below.

TABLE 16

| Bulk solution manufacture (Compounding tank) | | | |
|---|---|---|---|
| Production step | Process Parameter | Test (CQA) | Acceptance criteria |
| Dissolution of PVA | Temperature | Visual | Complete dissolution |
|  | Mixing speed/time | Dosage | TBD during the technical batch |
| Dissolution of Povidone | Mixing speed/time | Visual | Complete dissolution |
|  |  | Dosage | TBD during the technical batch |
| Dissolution of other excipients | Mixing speed/time | Visual | Complete dissolution |
| Dissolution of Lecithin | Mixing speed/time | Visual | Complete dissolution |
| pH adjustment of solution B | Mixing speed/time | pH measurement | 6.35 ± 0.05 |
| WFI QS |  | QS verification | 406.4 kg |
| Solution to be filtered (before 0.2 µm filtration into sterile holding tank) | Stirring Speed | Visual | Clear viscous solution |
|  |  | pH measurement | 5.6-6.7 |
|  |  | Bioburden determination | ≤10 CFU/100 ml |

TABLE 17

Aseptic storage of solution (Storage tank)

| Production step | Parameter | Test | Acceptance criteria |
|---|---|---|---|
| Tank sterilisation | Temperature/time | Sterilisation record | ≥121° C. 30 minutes |
| Storage tank cooling | Temperature | Temperature record | 20-25 ° C. |
| Sterile Filtration | Filter integrity | Integrity testing at the beginning of the transfer | Wetting agent: Exemplary Formulation 1<br>Pressure test: TBD<br>Air diffusion TBD<br>Nitrogen diffusion TBD<br>Wetting agent: Water<br>Pressure test: 2760 mbar<br>Air diffusion ≤ 12 ml/mn<br>Nitrogen diffusion ≤ 8 ml/mn |
| | | Integrity testing at the end of the transfer | Wetting agent: Exemplary Formulation 1<br>Pressure test: TBD<br>Air diffusion TBD<br>Nitrogen diffusion TBD<br>Wetting agent: Water<br>Pressure test: 2760 mbar<br>Air diffusion ≤ 12 ml/mn<br>Nitrogen diffusion ≤ 8 ml/mn |

TABLE 18

Filling operation

| Production Step | Parameter | Test | Acceptance criteria |
|---|---|---|---|
| Filling machine sterilisation | Temperature/time | Sterilisation record | ≥121° C. for 30 minutes |
| Before filling starting: Check of the packaging component conformity | Appearance | LDPE type<br>LDPE batch number<br>Mold format<br>Embossing on SDU | Complies |
| In the storage tank | Mix speed and pressure | Check of the storage tank | Low speed: to be defined<br>Pressure: >0 bar |
| At the beginning of filling | Format checking<br>Filled product checking | Engraving<br>Osmolality<br>pH<br>Appearance | Complies<br>250-330 mOsm/kg<br>5.6-6.7<br>Clear, viscous solution free from visible particles |
| During the filling operation | Appearance | SDU formation embossing readability Labelling readability No defect | Complies |
| | Functional tests | Opening Liquid flow | Complies |
| | Tightness | No leakage | 100% tight; untight SDUs are destroyed |
| | Filling weight | Periodic checking according to the MBR | ≥0.34 g |

TABLE 19

Labelling

| Labelling packaging step | Type of control | In-Process control test | Specification |
|---|---|---|---|
| Labelling | Visual check | Compliant labelling: item code, printing on packaging components, label position | Complies |
| | Visual check | Appearance of labelled doses: heads undamaged by labelling machine | Complies |

TABLE 20

| Secondary packaging | | | |
|---|---|---|---|
| Secondary packaging step | Type of control | In-Process control test | Specification |
| Over wrapping | Integrity/sealing<br>Appearance<br>Printing of variable data | Tightness<br>Visual<br>Visual | no leakage<br>Complies<br>Complies |

Sampling Plan

Table 21 below shows routine samples.

TABLE 21

| Routine Samples | | | | | |
|---|---|---|---|---|---|
| Sample type | Test | Number of samples | Laboratory in charge for analysis | Sample location | Sample frequency |
| Bulk solution | | | | | |
| Microbiological | Bioburden | 1 sample of 100 ml | XLV | Aseptic sampling between the prefilter and filter | Per solution batch |
| Filled SDU | | | | | |
| Analytical | Product appearance<br>pH<br>Osmolality<br>Viscosity<br>Appearance<br>Identification by RT<br>Viscosity<br>Surface Tension<br>Osmolality<br>pH<br>Particulate Matter<br>Assay-Polyvinyl Alcohol<br>Assay-Povidone | 11 blocks = 55 vials<br><br>50 blocks = 250 vials | XLV<br><br>Encompass | Across the filling run (at least at the beginning and at the end-10 vials every hour) | Per finished batch |
| Microbiological-sterility | Sterility test | 4 blocks of 5 vials = 20 vials | XLV | Across the filling run (including beginning, middle and end) | Per day * |

Table 22 shows extra samples for manufacturing process verification.

TABLE 22

| Bulk solution | | | | | |
|---|---|---|---|---|---|
| Sample type | Test | Number of samples | Laboratory in charge for analysis | Sample location | Sample frequency |
| Bulk solution | | | | | |
| Analytical | Product appearance<br>pH<br>Osmolality<br>Viscosity<br>Appearance<br>Identification by RT<br>Viscosity<br>Surface | 1 sample of 100 ml for XLV<br><br>100 ml for each sample (top/mid/ end of compounding) | XLV<br><br>Encompass | 1 sample top of compounding tank at the end of the compounding (before filtration) + At the sample port | On each registration batch |

TABLE 22-continued

| Bulk solution | | | | | |
|---|---|---|---|---|---|
| Sample type | Test | Number of samples | Laboratory in charge for analysis | Sample location | Sample frequency |
| | Tension Osmolality pH Assay-Polyvinyl Alcohol Assay-Povidone | for Encompass = 300 mL | | between the prefilter and the filter: 1 sample from top of compounding 1 sample from middle of compounding 1 sample from end of compounding | |
| Microbiological | Validation of Bioburden | 9 samples of 100 ml | XLV | In the compounding tank | On the 2 first batches |

TABLE 23

| Filled SDUs | | | | | |
|---|---|---|---|---|---|
| Sample type | Test | Number of samples | Laboratory in charge for analysis | Sample location | Sample frequency |
| Filled SDU | | | | | |
| Analytical | Product appearance pH Osmolality Viscosity | 15 blocks = 75 vials per sampling point | XLV | Beginning of the drain of the filling machine End of the drain of the filling machine At the beginning of the filling, when the volume are adjusted At 50% of the filling At the end of the filling | Per registration batch |
| Analytical | Appearance Identification by RT Viscosity Surface Tension Osmolality pH Assay-Polyvinyl Alcohol Assay-Povidone | 50 blocks = 250 vials per sampling point | Encompass | At the beginning of the filling, At 50% of the filling At the end of the filling | Per registration batch |
| Microbiological | Validation of Sterility | 60 blocks = 300 vials | XLV | At 50% of the filling | On the 2 first batches |
| | Sterility | 10 blocks = 50 vials | | At the beginning of the filling, when the volume are adjusted | Per registration batch |

TABLE 23-continued

| | | | Filled SDUs | | |
|---|---|---|---|---|---|
| Sample type | Test | Number of samples | Laboratory in charge for analysis | Sample location | Sample frequency |
| | | | | At 50% of the filling At the end of the filling | |

Filling volumes checking, control of appearance and opening of the doses were performed regularly throughout the manufacture. Integrity or leak tests of the doses were performed at 100%. These were IPCs. The results were recorded in the batch record.

Analysis of the extra samples was performed on the first technical batch as seen in Tables 24-26.

TABLE 24

| | Extra sample for filter determination | | | |
|---|---|---|---|---|
| Sample type | Test | Number of samples | Sample location | Sample frequency |
| Bulk solution Analytical | Filter validation | 1 sample of 6 L | top of compounding tank at the end of the compounding: | On the 1$^{st}$ technical batch |

TABLE 25

| | Extra samples for stability study | | | |
|---|---|---|---|---|
| Sample type | Test | Number of samples | Sample location | Sample frequency |
| Filled single dose unit Analytical | Appearance Identification by RT Viscosity Surface Tension Osmolality pH Assay-Polyvinyl Alcohol Assay-Povidone Particulate Matter Sterility Weight Loss/Gain Dye Ingress | 700 vials = 140 blocks per sampling point | At the beginning of the filling, when the volume are adjusted At 50% of the filling At the end of the filling | Per registration batch |

TABLE 26

| | In process control specifications | |
|---|---|---|
| | Test | Acceptance criteria |
| IPC1 (Ph adjustment) | pH | 6.30-6.40 |
| IPC2 (compounding solution) | Product appearance Viscosity Osmolality pH Bioburden | Clear viscous solution 4-10 cps 250-330 mOsm/kg 5.6-6.7 |

TABLE 26-continued

| | In process control specifications | |
|---|---|---|
| | Test | Acceptance criteria |
| IPC3 (during filling step) | Bacteria aerobic Bacteria anaerobic Yeasts and molds Product appearance Viscosity Osmolality pH Filling weight | ≤10 CFU/100 mL ≤10 CFU/100 mL ≤10 CFU/100 mL Clear viscous solution 4-10 cps 250-330 mOsm/kg 5.6-6.7 NLT 0.34 g |

Product Specifications

TABLE 27

| Product Specifications | |
|---|---|
| Test | Acceptance Criterion |
| Appearance | Clear viscous solution |
| Viscosity | 4.0-10.0 cPs |
| Osmolality | 250-330 mOsm/kg |
| pH | 5.6-6.7 |
| Identification by RT | Conforms |
| Surface Tension | 40.0-55.0 dynes/cm |
| Povidone (Polyvinyl Pyrrolidone): 2% | NLT 90.0% and NMT 110.0% of label |
| Polyvinyl Alcohol: 2.7% | NLT 75.0% and NMT 125.0% of label |
| Particulate Matter | ≥10 μm: NMT 50 per mL ≥25 μm: NMT 5 per mL ≥50 μm: NMT 2 per mL |
| Sterility | Meets the USP<71> |
| Product Specifications | |
| Test | Acceptance Criterion |
| Product appearance | Clear viscous solution |
| Viscosity | 4-10 cps |
| Osmolality | 250-330 mOsm/kg |
| pH | 5.6-6.7 |
| Bioburden | |
| Bacteria aerobic | ≤10 CFU/100 mL |
| Bacteria anaerobic | ≤10 CFU/100 mL |
| Yeasts and molds | ≤10 CFU/100 mL |
| Sterility | Meets the USP <71> |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What we claim is:

1. A composition stored in a dropper bottle, the composition consisting of:
   (a) povidone;
   (b) fully hydrolyzed polyvinyl alcohol;
   (c) partially hydrolyzed polyvinyl alcohol;
   (d) sodium chloride;
   (e) boric acid;
   (f) disodium edetate dihydrate;
   (g) potassium chloride;
   (h) glycerin;
   (i) ethyl alcohol;
   (j) lecithin;
   (k) polysorbate 80;
   (l) a pH adjusting agent; and
   (m) water;
   wherein the fully hydrolyzed polyvinyl alcohol has a molecular weight in a range of 20,000 to 200,000 daltons; the composition is an ophthalmic composition; and the composition is preservative free.

2. The composition of claim 1, wherein a concentration of the povidone is 1% w/v to 5% w/v.

3. The composition of claim 1, wherein a concentration of the fully hydrolyzed polyvinyl alcohol is 0.5% w/v to 5% w/v.

4. The composition of claim 1, wherein a concentration of the partially hydrolyzed polyvinyl alcohol is 0.5% w/v to 5% w/v.

5. The composition of claim 1, wherein a concentration of the fully hydrolyzed polyvinyl alcohol and the partially hydrolyzed polyvinyl alcohol is no more than 4% w/v.

6. The composition of claim 1, wherein the fully hydrolyzed polyvinyl alcohol has a molecular weight in a range of 80,000 to 200,000 daltons.

7. The composition of claim 1, wherein the partially hydrolyzed polyvinyl alcohol has a molecular weight in a range of 1,000 to 50,000 daltons.

8. The composition of claim 1, wherein the pH adjusting agent is at least one selected from the group consisting of hydrochloric acid and sodium hydroxide.

9. The composition of claim 7, wherein the partially hydrolyzed polyvinyl alcohol has a molecular weight in a range of 10,000 to 50,000 daltons.

10. The composition of claim 1, wherein a concentration of sodium chloride is 0.1% w/v to 1% w/v.

11. The composition of claim 1, wherein a concentration of boric acid is 0.1% w/v to 1% w/v.

12. The composition of claim 1, wherein a concentration of disodium edetate dihydrate is 0.01% w/v to 1% w/v.

13. The composition of claim 1, wherein a concentration of potassium chloride is 0.01% w/v to 1% w/v.

14. The composition of claim 1, wherein a concentration of glycerin is 0.001% w/v to 1% w/v.

15. The composition of claim 1, wherein a concentration of ethyl alcohol is 0.001% w/v to 0.5% w/v.

16. The composition of claim 1, wherein a concentration of lecithin is 0.001% w/v to 0.5% w/v.

17. The composition of claim 1, wherein a concentration of polysorbate 80 is 0.01% w/v to 1% w/v.

18. The composition of claim 1, wherein
    a concentration of the povidone is 1% w/v to 5% w/v;
    a concentration of the fully hydrolyzed polyvinyl alcohol is 0.5% w/v to 5% w/v;
    a concentration of the partially hydrolyzed polyvinyl alcohol is 0.5% w/v to 5% w/v;
    a concentration of sodium chloride is 0.1% w/v to 1% w/v;
    a concentration of boric acid is 0.1% w/v to 1% w/v;
    a concentration of disodium edetate dihydrate is 0.01% w/v to 1% w/v;
    a concentration of potassium chloride is 0.01% w/v to 1% w/v;
    a concentration of glycerin is 0.001% w/v to 1% w/v;
    a concentration of ethyl alcohol is 0.001% w/v to 0.5% w/v;
    a concentration of lecithin is 0.001% w/v to 0.5% w/v; and
    a concentration of polysorbate 80 is 0.01% w/v to 1% w/v.

19. The composition of claim 1, wherein a pH of the composition is no more than 6.6.

20. The composition of claim 1, wherein an osmolality of the composition is 200 mOsm/kg to 400 mOsm/kg.

21. The composition of claim 1, wherein the dropper bottle comprises a squeezable container provided with a tapered dispenser that terminates in a discharge aperture.

22. The composition of claim 21, wherein the dropper bottle has a volume of 10 mL.

* * * * *